United States Patent [19]
Leung et al.

[11] Patent Number: 5,985,926
[45] Date of Patent: Nov. 16, 1999

[54] METHOD FOR INHIBITING INTRACELLULAR VIRAL REPLICATION

[75] Inventors: David W. Leung, Mercer Island, Wash.; Gail E. Underiner, Malvern, Pa.; Jack W. Singer, Seattle, Wash.

[73] Assignee: Cell Therapeutics, Inc., Seattle, Wash.

[21] Appl. No.: 08/797,326

[22] Filed: Feb. 10, 1997

Related U.S. Application Data

[63] Continuation of application No. 08/147,255, Nov. 1, 1993, abandoned, and a continuation of application No. 08/333,575, Nov. 1, 1994, abandoned.

[51] Int. Cl.$^6$ .................................................. A61K 31/20
[52] U.S. Cl. ....................... 514/558; 514/258; 514/262; 514/274; 514/299; 514/315; 514/418; 514/425; 514/529; 514/552; 514/561; 514/613; 514/617; 514/626; 514/629; 514/669
[58] Field of Search .................................... 514/558, 258, 514/262, 274, 299, 315, 418, 425, 529, 552, 561, 613, 617, 626, 629, 669

[56] References Cited

U.S. PATENT DOCUMENTS

| | | | |
|---|---|---|---|
| 5,470,878 | 11/1995 | Michnick et al. ...................... | 514/558 |
| 5,585,380 | 12/1996 | Bianco et al. .......................... | 514/263 |

FOREIGN PATENT DOCUMENTS

| | | |
|---|---|---|
| WO 95/12396 | 5/1995 | WIPO . |
| WO 95/13808 | 5/1995 | WIPO . |

OTHER PUBLICATIONS

Folch et al., "A Simple Method for the Isolation and Purification of Total Lipids from Animal Tissues", McLean Hospital Research Laboratories, (1956) pp. 497–509.
Bligh et al., "Canadian Journal of Biochemistry and Physiology", The National Research Council of Canada, vol. 37, No. 8, (1959), pp. 911–917.
Sodrosky et al., "Trans–acting Transcriptional Regulation of Human T–Cell Leukemia Virus Type III Long Terminal Repeat", Science, vol. 227, (1985), pp. 171–173.
Schooley, "Cytomeagalovirus in the Setting of Infection with Human Immunodeficiency Virus", Reviews of Infectious Diseases, vol. 12, (1990), pp. 5811–5819.
Varmus, "Regulation of HIV and HTLV Gene Expression", Genes and Development, vol. 2, (1988), pp. 1055–1062.
Walker et al., "CD8+ Lymphocytes Can Control HIV Infection in Vitro by Suppressing Virus Replication", Science, vol. 234, (1986).
Peterson et al., "Human Cytomegalovirus–stimulated Peripheral Blood Mononuclear Cells Induce HIV–1 Replication via a Tumor Necrosis Factor–a–mediated Mechanism", J. Clin. Invest., vol. 89, (1992) pp. 574–580.
Frankel et al., "Cellular Uptake of the Tat Protein from Human Immunodeficiency Virus", Cell, vol. 55, (1988), pp. 1189–1183.
Haseltine, "Molecular Biology of the Human Immunodeficiency Virus Type 1", the FASEB Journal, vol. 5, (1991), pp. 2349–2360.

Brinchmann et al., "CD8+ Inhibit HIV Replication in Naturally Infected CD4+T Cells: Evidence for a Soluble Inhibitor" The Journal of Immunology, vol. 144, (1990), pp. 2961–2966.
Berger et al., "Secreted Placental Alkaline Phosphatase: A Powerful new Quantitative Indicator of Gene Expression in Eukaryotic Cells", Gene, vol. 66, (1988), pp. 1–10.
Andrieu et al., "Effects of Cyclosporin on T–Cell Substes in Human Immunodeficiency Virus Disease", Clinical Immunology and Immunopathology, vol. 46, (1988), pp. 181–198.
Cerny et al., "Protective Effect of Cycolsporin A On Immune Abnormalities Observed in the Murine Acquired Immunodeficiency Syndrome", Eur. J. Immunol., vol. 21, (1991), pp. 1747–1750.
Cullen, "Regulation of HIV–1 Gene Expression", FASBE Journal, vol. 5, (1991), pp. 2361–2368.
Fauci, "Multifactorial Nature of Human Immunodeficiency Virus Disease: Implications for Therapy", Science, vol. 262, (1993), pp. 1011–1018.
Gougeon et al., "Apoptosis in AIDS", Science, vol. 260, (1993), pp. 1269–1270.
Weiss, "How Does HIV Cause AIDS", Science, vol. 260, (1993), pp. 1273–1278.
Hsu et al., "Inhibition of HIV Replication in Acute and Chronic Infections in Vitro by a Tat Antagonist", Science, vol. 254, (1991), pp. 1799–1802.
Pantaleo et al., "HIV Infection is Active and Progressive in Lymphoid Tissue During the Clinically Latent Stage of Disease", Nature, vol. 362, (1993), pp. 355–358.
Bass et al., "Immune Changes in HIV–1 Infection: Significant Correlations and Differences in Serum Markers and Lymphoid Phenotypic Antigens", Clinical Immun. and Immunopath. vol. 64, No. 1, (1992), pp. 63–70.
Jones et al., "Control of RNA Initiation and Elongation at the HIV–1 Promoter", Annu. Rev. Biochem., vol. 63, (1994), pp. 717–43.
Gaynor, "Cellular Transcription Factors Involved in the Regulation of HIV–1 Gene Expression", AIDS, vol.6, (1992), pp. 347–636.

(List continued on next page.)

*Primary Examiner*—Keith D. MacMillian
*Attorney, Agent, or Firm*—Foley & Lardner

[57] ABSTRACT

There is disclosed a method of preventing or delaying the occurrence of acquired immunodeficiency syndrome (AIDS) in human immunodeficiency virus (HIV) seropositive humans by administering an effective amount of a compound that inhibits cellular signaling through a specific phospholipid-based cellular signaling and signal amplification pathway. The invention further provides a method for preventing or delaying clinical symptoms of a group of viral diseases wherein the viral disease is mediated by host cell viral replication. The invention provides an advantage by attacking host cellular signaling mechanisms to prevent the development of drug resistance from rapidly mutating viruses.

14 Claims, 25 Drawing Sheets

OTHER PUBLICATIONS

Rosenberg et al., "Induction of Expression of HIV in Latently or Chronically Infected Cells", AIDS Research and Human Retroviruses, vol. 5, No. 1, (1989), pp. 1–4.

Kaltschmidt et al., "Constitutive NF–kb Activity in Neurons", Molecular and Cellular Biology, vol. 14, No. 6, (1994), pp. 3981–3992.

Various, "Letters to the Editor", The Lancet, vol. 341, (1993), pp. 889–890.

Lu et al., "Identification of cis–Acting Repressive Sequences within the Negative Regulatory Element of Human Immunodeficiency Virus Type 1", Journal of Virology, vol. 64, No. 10, (1990), pp. 5226–5229.

Dignam et al., "Accurate Transcription Initiation by RNA Polymerase II in a Slouble Extract From Isolated Mammalian Nuclei", vol. 11, No. 5, (1983), pp. 1475–1489.

Poli et al., "Cytokine Modulation of HIV Expression", Immunology, vol. 5, (1993), pp. 165–173.

Hsu et al., "Inhib. of Type 1 Human Immunodeficiency Virus Replication by a Tat Antagonist to Which the Virus Remains Sensitive After Prolonged Exposure in Vitro", Proc. Natl. Acad. Sci., vol. 90, (1993), pp. 6395–6399.

Brighty et al., "Envelope Proteins from Clinical Isolates of Human Immuno. Virus Type 1 That are Refractory to Neutral. by Sol. CD4 Possess High Affin. for CD4 Receptor", Proc. Natl. Acad. Sci., vol 88, pp. 7802–7805, (1991).

Zeichner, "The Molecular Biology of HIV", Perinatal AIDS, vol. 21, No. 1, (1994), pp. 39–73.

Carthew et al., "An RNA Polymerase II Transcription Factor Binds to an Upstream Element in the Adenovirus Major Late Promoter", Cell, vol. 43, (1985), pp. 439–448.

Hawa et al., "Post–transcriptional Regulation of Bovine Parathyoid Hormone Systhesis", Hormone Synthesis, Journal of Molecular Endocrin., vol. 10, (1993), pp. 43–49.

Clouse et al., "Viral Antigen Stimulation of the Production of Human Monokines Capable of Regulating HIV1 Expression", Journal of Immunology, vol. 143, (1989), pp. 470–475.

Poli et al., "Interleukin 6 Induces Human Immuno. Virus Exp. in Infected Monocytic Cells Alone Synergy Tumor Necrosis Factor Transcrip. & Post–Transcrip. Mechan.", J. Exper. Med., vol. 172, (1990), pp. 151–158.

Morandi et al., "Proinfalmmatory Cytokines (Interleukin–1B and Tumor Necrosis Factor–a) Down Regulate Synthesis & Secretion Thromb. Human Endo. Cells", J. Cell Phys., vol. 160, (1994), pp. 367–377.

Rhoads, "Regulation of Eukaryotic Protein Synthesis by Initiation Factors", Journal of Biol. Chem., vol. 268, No. 5, (1993), pp. 3017–3020.

Tate et al., "Secreted Alkaline Phosphatase: An Internal Standard for Expression of Injected mRNAs in the Xenopus OOcyte", FASBE Journal, vol. 4, (1990), pp. 227–231.

Pfeifer et al., "Genomic Sequencing and Methylation Analysis by Ligation Mediated PCR", Science, vol. 246, (1989), pp. 810–813.

Poli et al., "Interleukin 1 Induces Expression of the Human Immunodeficiency Virus Alone and in Synergy with Interleukin. . . ", Proc. Natl. Acad. Sci., vol. 91, (1994), pp. 108–112.

Baeuerle et al., "Function and Activation of NF–kB in the Immune System", Annu. Rev. Immunol., vol. 12, (1994), pp. 141–179.

Nabell et al., "Human Immunodeficiency Virus 1 Tat Stimulates Transcription of the Transforming Growth Factor. . . ", Cell Growth & Differentiation, vol. 5, (1994), pp. 87–93.

van Kessel et al., "High Performance Liquid Chromatographic Separation and Direct Ultraviolet Detection of Phospholipids", Biochimia et Biophysica Acta, vol. 486, (1977), pp. 524–530.

Yoshida et al., "New Preparation Method for 9–Anthryldiazomethane (ADAM) as a Fluorescent Labeling Reagent for Fatty Acids and Derivatives", Analytical Biochem., vol. 173, (1988), pp. 70–74.

Ito et al., "Interleukin 3 Stimulates Protein Synthesis by Regulating Double–Stranded RNA–dependent Protein Kinase", Proc. Natl. Acad. Sci., vol. 91, (1991), pp. 7455–7459.

Folks et al., "Cytokine–Induced Expression of HIV–1 in a Chronically Infected Promonocyte Cell Line", Science, vol. 238, pp. 800–802, 1993.

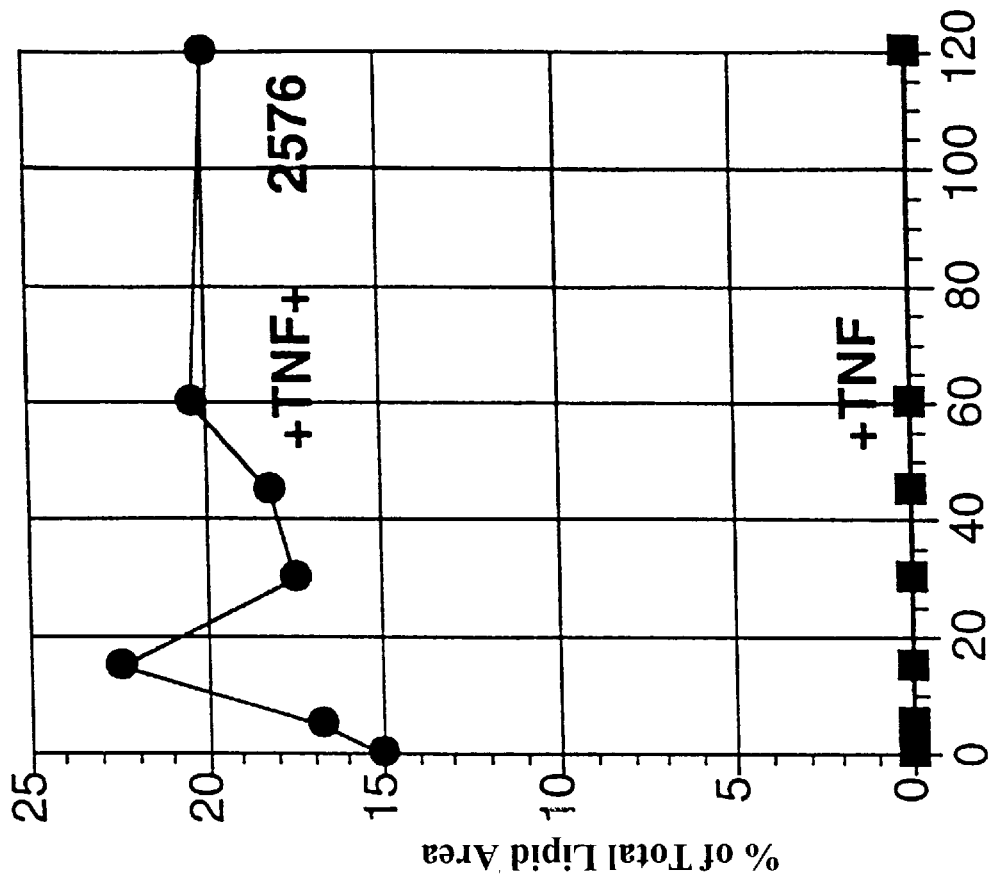
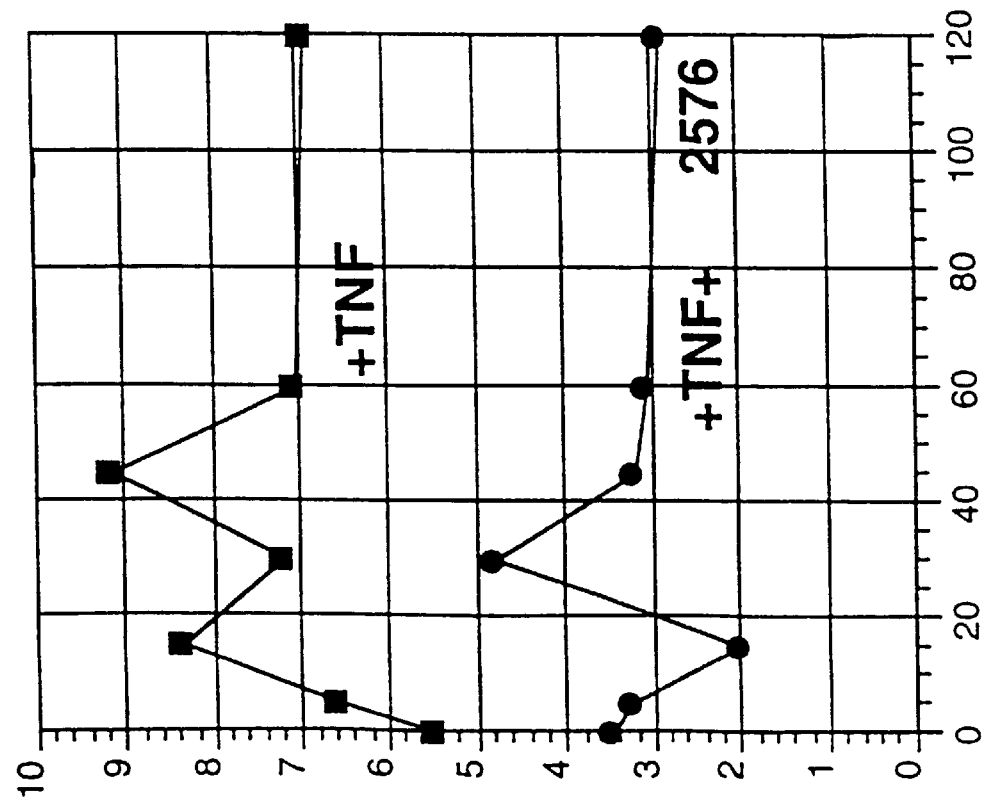
FIG. 21B
FIG. 21A

METHOD FOR INHIBITING INTRACELLULAR VIRAL REPLICATION

CROSS REFERENCE TO RELATED APPLICATION

This patent application is a continuing application from U.S. patent application Ser. No.08/147,255 filed on Nov. 1, 1993 abandoned and U.S. patent application Ser. No. 08/333,575 filed on Nov. 1, 1994 abandoned.

TECHNICAL FIELD OF THE INVENTION

The invention provides methods of preventing or delaying the occurrence of acquired immunodeficiency syndrome (AIDS) in human immunodeficiency virus (HIV) seropositive humans by administering an effective amount of a compound that inhibits cellular signaling through a specific phospholipid-based cellular signaling and signal amplification pathway. The invention further provides methods for preventing or delaying clinical symptoms of a group of viral diseases wherein the viral disease is mediated by host cell viral replication. The invention provides an advantage by attacking host cellular signaling mechanisms to prevent the development of drug resistance from rapidly mutating viruses.

BACKGROUND OF THE INVENTION

Drugs currently approved for AIDS therapy belong to classes of compounds that directly attack viral proteins, such as reverse transcriptase (e.g., AZT or zidovudine) or HIV protease. Such compounds have the problem of rapidly developing drug resistance due to rapid transformation of the infecting viral genome. However, despite the problem of rapid drug resistance, such drugs have been used to treat HIV seropositive individuals to help prevent the spread and progression of the infection into the clinical symptoms of AIDS. This problem is exemplified by a recent clinical study (Aboulker et al., Lancet 341:889–890, 1993) showing that AZT treatment of asymptomatic patients in early stages of HIV infection showed no delay in the progression of AIDS disease, although a consistently higher number of CD4$^+$ T cells was observed in the treatment group when compared to the placebo group, suggesting that CD4 may not be a good marker for AIDS drug efficacy and the need for other approaches for the treatment of AIDS.

HIV infection leads to progressive depletion of CD4+ T lymphocytes and eventual development of clinical symptoms associated with AIDS. After the primary HIV infection, there is a prolonged incubation period of clinical latency that can last as long as twelve years (Weiss, Science 260:1273–1279, 1993). Recent studies indicate viral replication occurs continuously (Pantaleo et al., Nature 362:355–358, 1993) and multiple components of the immune system are chronically activated (Fauci, Science 262:1011–1018, 1993; Bass et al., Clin Immunol Immunopathol. 64:63–70, 1992) during this asymptomatic phase of disease. Persistent activation of the immune system may lead to overproduction of a number of cytokines (Fauci, Science 262:1011–1018, 1993), induction of HIV expression in latently infected cells (Rosenberg et al., AIDS Res. Hum. Retroviruses 5:1–4, 1989), and apoptosis of T cells (Gougeon, Science 260:1269–1270, 1993). Like other retroviruses, all the genes of HIV are expressed under the control of the long terminal repeat (LTR) promoter through multiply spliced mRNAs and precursor proteins that are processed into individual products (Zeichner, Clin. Perinatol. 21:39–73, 1994). Unique DNA and RNA elements in the HIV LTR make this region a target for regulation by many cellular transcription factors as well as the HIV transactivator protein tat (Gaynor, AIDS 6:347–363, 1992; and Jones et al., Annu. Rev. Biochem. 63:717–743, 1994). The LTR promoter contains cis-acting repressive sequences that inhibit HIV transcription initiation in resting T cells (Lu et al., J. Virol. 64:5226–5229, 1990). Mitogenic stimulation of T cells can activate the LTR promoter to synthesize large amounts of viral RNA. Cytokines, such as tumor necrosis factor (TNF-α) and interleukin-6 (IL-6), are known to induce HIV synthesis in infected cells (Poli et al., Semin Immunol. 5:165–173, 1993).

HIV infection leads to progressive depletion of specific populations of T lymphocytes and progression of the infection to clinical symptoms associated with AIDS (acquired immunodeficiency syndrome), including HIV-related dementia. Currently, there is no effective treatment for HIV-related dementia, although current therapy, AZT, may have some minor short-term effectiveness.

Microglial cells and TNFα production have been implicated in the neuropathogenesis of HIV-related dementia. Moreover, microglia and TNFα release have been suggested to play a role in other neurodegenerative disorders, such as Alzheimer's disease and multiple sclerosis.

The use of immunosuppressive and immunomodulatory agents have been shown to suppress viral replication. Specifically, immunomodulating CD8 lymphocytes have been shown to suppress replication of HIV in peripheral blood mononuclear cells (Walker et al., Science 234:1563, 1986) and activated CD8+ T cells have been shown to inhibit replication of HIV in cultures of CD4+ cells from asymptomatic HIV seropositive individuals (Brinchmann et al., J. Immunol. 144:2691, 1990). Further, the immunosuppressive compound, cyclosporin A (CyA) has a protective effect in several animal models of viral infection. Specifically, chronic treatment with CyA before and after infection with LP-BM5 murine leukemia virus was effective against the development of immunodeficiency disease (Cerny et al., Eur. J. Immunol. 21:1747, 1991). There is also evidence that CyA increases T4 cells and inhibits lymphadenopathy in AIDS and HIV-seropositive, non-AIDS patients (Andrieu et al., Immunol. Immunopath. 46:181, 1988).

The HIV genome encodes at least seven groups of viral proteins (Haseltine, FASEB 5:2349, 1991). These groups of proteins include the three classes of polypeptides present in the majority of animal retroviruses: (1) structural, nonenvelope polypeptides encoded by the gag gene; (2) enzymes required for virion replication (reverse transcriptase/rt) and for cleavage of viral precursor proteins (protease/pr), both encoded by the pol gene; and (3) envelope polypeptides encoded by the env genes. In addition, HIV's possess genes that encode four sets of polypeptides not found in the majority of typical retroviruses. These include a transactivating regulator of RNA translation (tat), a cis-acting downregulator of RNA transcription (nef), a regulator that modulates the expression of structural proteins (rev), a protein that modulates viral infectivity (vif), and two proteins (vpr, vpu) whose functions are still unclear. The genomic order of viral genes encoding the initial portion of each of these proteins (5' to 3') is gag-pr-pol-vif-tat-rev-env-nef.

There are a number of models for predicting the effectiveness of a particular therapy for preventing the progression of HIV infection into an AIDS syndrome and related HIV-related dementia. One such key indicator is the tat protein of HIV type 1 (HIV-1), which is a potent transactivator of expression of genes from the viral long term repeat (LTR) in vitro, and is essential for viral replication and virus-mediated cytopathicity (Varmus, *Genes Dev.* 2:1055, 1988 and Cullen, *FASEB J.* 5:2361, 1991). Tat appears to exert its effect through novel mechanisms that depend upon the recognition of specific, structured, cis-acting viral DNA sequences.

The tat gene encodes a 14 kD protein that transactivates and increases transcription of DNA in HIV-infected cells. The tat gene consists of two separate segments that have been mapped to a location in the HIV genome between the vif and nef regions. It encodes for a 14 kD protein that exists as a metal-linked dimer in infected cells. Products of the tat gene have been shown to greatly augment the rate of viral protein synthesis in HIV-infected cells, and thus to increase the production of HIV virions.

Viral replication of a large number of classes of viruses occurs in a host cell and is often accelerated by primary inflammatory mediators, such as tumor necrosis factor (TNF) (Poli et al., *Proc Natl. Acad. Sci. USA* 87:782, 1990). Therefore, if a drug were able to ablate or significantly diminish the signal to replicate in a virally infected host cell, such a drug could conceivably block the progression of a virus-based disease in a large number of indications. The invention was made in an effort to find such a drug that acts by such a mechanism of action to have broad spectrum antiviral activity directed toward blocking propagation of the virus but not directly cytotoxic to the virus.

Therefore, there is also a need in the art to develop therapeutic compounds for HIV infection that can block the progression of the disease by acting intracellularly to prevent formation of the tat protein and thereby prevent virion assembly within an infected cell. This invention follows a discovery concerning a functional class of compounds that inhibit a specific group of phospholipid-based second messenger signal amplification pathways also inhibit transactivation of HIV-LTR promoter by tat protein with minimal cytotoxic effects.

SUMMARY OF THE INVENTION

The invention provides methods for treating viral infection by preventing viral replication, viral gene expression and release of certain viral antigens in infected cells by inhibiting host cell viral replication signaling, comprising administering an effective amount of a compound that inhibits formation of myristilated PA (Phosphatidic acid) in response to an inflammatory stimulus. An inflammatory stimulus can be mediated by, for example, TNF or IL-1. The compound that can inhibit myristilated PA (myrPA) in either the sn-1 or sn-2 positions or both can be determined by following an assay procedure described herein. Preferably, the compound is a small organic molecule that can mimic binding to a complex of enzymes that mediate signal amplification. The compounds include resolved enantiomers and/or diastereomers, hydrates, salts, solvates and mixtures thereof, wherein the compounds have a straight or branched aliphatic hydrocarbon structure of the general formula:

In this general formula j is an integer from one to three. $R_4$ is a terminal moiety comprising a substituted or unsubstituted, carbocyclic or heterocyclic moiety or open chain analogs thereof. When $R_4$ is a heterocyclic moiety, it consists essentially of one to three ring structures having 5–7 members each, a heteroatom, and a predominantly planar structure or essentially aromatic.

X of the general formula is a racemic mixture or R or S enantiomer of:

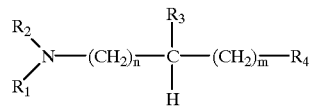

wherein n is an integer from one to four and m is an integer from four to twenty. $R_1$ and $R_2$ are hydrogen, a straight or branched chain alkyl, alkenyl or alkynyl of up to twenty carbon atoms in length or —$(CH_2)_w R_5$. Optionally, $R_1$ and $R_2$ may jointly form a substituted or unsubstituted, saturated or unsaturated heterocycle having from four to eight carbon atoms. $R_3$ is hydrogen, a hydroxy group, a $C_{1-3}$ straight or branched alkyl, or a $C_{1-3}$ alkoxy.

$R_5$ is an hydroxyl, halo, $C_{1-8}$ alkoxyl group or a substituted or unsubstituted carbocycle or heterocycle. $R_5$ can be a substituted or unsubstituted aryl group wherein the substituted aryl group is mono, di or tri substituted with hydroxy, chloro, fluoro, bromo, or alkoxy (C1-6) substituents, or

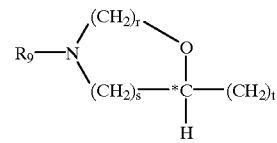

$R_9$ is a hydrogen or a straight or branched chain alkane or alkene of up to eight carbon atoms in length, —$(CH_2)_m R_5$. Alternatively, $R_9$ forms a cyclo saturated or unsaturated aromatic ring or substituted aromatic ring having from four to eight carbon atoms and including the nitrogen atom within the ring. r and s are independently integers from one to four, the sum (r+s) is not greater than five. One or more carbon atoms in $(CH_2)_r$ or $(CH_2)_s$ may be substituted by a keto or hydroxy group, t is an integer from one to fourteen, and $R_5$ is a substituted or unsubstituted aryl group wherein the substituted aryl group is mono, di or tri substituted with hydroxy, chloro, fluoro, bromo, or alkoxy (C1-6) substituents.

Alternatively, X is independently a resolved enantiomer ω-1 secondary alcohol-substituted alkyl ($C_{5-8}$) substantially free of the other enantiomer, or X is a branched —$(CH_2)$a-$CHR_6$—$(CH_2)$b-$R_7$, wherein a is an integer from about 4 to about 12, b is an integer from 0 to 4, $R_6$ is an enantiomer (R or S) or racemic mixture ($C_{1-6}$) alkyl or alkenyl, and $R_7$ is a hydroxy, keto, cyano, chloro, iodo, flouro, or chloro group.

Preferred compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+a number of carbon atoms in the linking carbon chain being less than six.

In the compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, heterocyclic moiety, wherein the heterocyclic moiety consists essentially of one to three ring structures having 5–7 members each, a heteroatom, and a predominantly planar structure or essentially aromatic. However, if $R_4$ is phthalimide, m of formula I is not less than five.

The compounds may include resolved enantiomers and/or diastereomers, hydrates, salts, solvates and mixtures thereof that have a straight or branched aliphatic hydrocarbon structure of formula II:

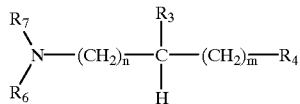

In the above formula II, n, m, $R_3$, and $R_4$ are defined as provided in formula I above. $R_6$ and $R_7$ are hydrogen, a straight or branched chain alkane, alkene or alkyne of up to twenty carbon atoms in length, or $—(CH_2)_xR_8$, at least one of $R_6$ or $R_7$ being $—(CH_2)_xR_8$. In formula II, x is an integer from zero to fourteen and $R_8$ is a moiety having a general structure as provided in formula III:

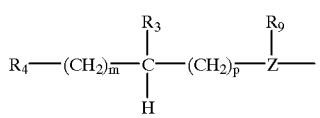

In formula III, above, m, $R_3$, and $R_4$ are defined as provided in formula I above. Z is N or CH and p is an integer from zero to four. $R_9$ is H or a straight or branched chain alkane, alkene or alkyne of up to twenty carbon atoms in length.

The invention provides methods for treating viral infections by attacking host cell mechanisms that contribute to intracellular viral replication and viral gene expression without attacking directly any viral proteins involved in viral replication. Methods specific to AIDS, HIV infection, and CMV infections are provided. By targeting a host cell signaling mechanism, the illustrated compounds provide an unexpected advantage of avoiding drug resistance from rapid viral mutation that has plagued current AIDS therapies that attack viral reverse transcriptase and protease enzymes. Moreover, the compounds are active against a very wide range of retroviruses and other viruses because there is no need for viral specificity when targeting common host cell mechanisms. However, the method of treatment is designed to prevent further progression of the virally-mediated disease but not to eradicate the virus. Therefore, the present inventive method includes combination therapeutic regimens that combine an agent designed to prevent host cell viral replication by targeting host cell signaling together with an agent or group of agents that are directly antiviral.

The compounds described herein exert their antiviral activity by inhibiting one or a plurality of enzymes or an enzyme complex, resulting in a diminution of host (or infected) cell PA (phosphatidic acid) formation in response to an inflammatory stimulus (e.g., TNF or IL-1) mediated through a Type I TNF or IL-1 receptor on the host cell surface. Therefore, the inventive compounds describe a genus of compounds that share a common mechanism of action, on a cellular level, that results in decreased intracellular signaling within a virally-infected cell, that does not transmit an inflammatory signal that would otherwise (in the absence of drug) signal an infected cell to begin the process of viral replication, gene expression, assembly and virion shedding. This cellular and biochemical mechanism of action, as illustrated by cells infected by the HIV virus as described herein, provides evidence for a general antiviral activity of the genus of compounds described herein, or other compounds that exert a similar mechanism of action (that is, prevention of infected host cell PA accumulation in response to an inflammatory stimulus) by virtue of the ability of the drug to prevent normal viral replication, gene expression and p24 release within an infected host cell.

Examples of other viruses that also replicated in an infected host cell in response to inflammatory stimuli (usually mediated by the cytokines TNF or IL-1) include, for example, cytomegalovirus (CMV), herpes family of viruses, including herpes simplex virus (HSV) 1, 2 and 6, hepatitis A, B, C and D, HIV 1 and 2, Epstein Barr virus (EBV), human T cell leukemia virus (HTLV), human papilloma virus, influenza, parainfluenza, respiratory syncytial virus, all adenoviruses, and rhinoviruses. Therefore, the inventive method results in prevention of progression and treatment of a viral disease, comprising administering an effective amount of a compound that can reduce intracellular myrPA concentrations in response to an inflammatory stimulus. Examples of viral diseases include, for example, CMV retinitis, AIDS, ARDS, systemic viral diseases affecting immunocompromised individuals (e.g., AIDS or transplant recipients), cold sores (HSV-1), genital herpes (HSV-2), hepatitis (A, B or C, or HSV-6), genital warts (human papiloma virus), infectious mononucleosis and some lymphomas (EBV), shingles (*Varicella zoster*), pericarditis (coxsackie virus), influenza, and cold and flu (rhinoviruses and adenoviruses). As a result of the inventive method to inhibit the progression of a viral disease caused by retroviruses and related families of DNA viruses, the inventive method further provides methods for treating a consequence of viral infection of the retroviral variety, wherein consequences of retroviral infections include, but are not limited to, cachexia associated with HIV infection, cachexia associated with EBV infection, HIV, EBV and HTLV related malignancies such as Kaposi's sarcoma and lymphoma, AIDS-related opportunistic infections (PCP, MAI, etc.) and for prophylaxis of opportunistic infection in AIDS patients.

BRIEF DESCRIPTION OF THE DRAWINGS

FIG. 12 (bottom panel) shows the effect of several compounds on TNFα-mediated upregulation of HIV-1 in U1 cells. TNFα is a potent stimulus of viral expression. Again, CT1501R, CT1829, CT1411 and CT2576 all suppressed HIV-1 expression, but CT2576 was the most effective and CT1829 showed some cytotoxicity at a 25 µM concentration.

FIG. 21 shows two graphs for peak D (a measure of various PA species in an HPLC separation) and Peak A5 (a measure of lyso (bis) PA species) with EB293 cells (human embryonic origin) stimulated with human TNF (20 ng/ml, Genzyme) with or without treatment with CT2576 (10 $\mu$M.). The left panel shows that drug treatment reduced PA mass across all time points measured, indicating inhibition of formation of PA species to acceleration of PA species metabolism. However, when considering the right hand graph showing increased lyso (bis) PA species across all time points, the CT2576 activity inhibits PA formation from lyso (bis) PA species.

DETAILED DESCRIPTION OF THE INVENTION

Figure 1:
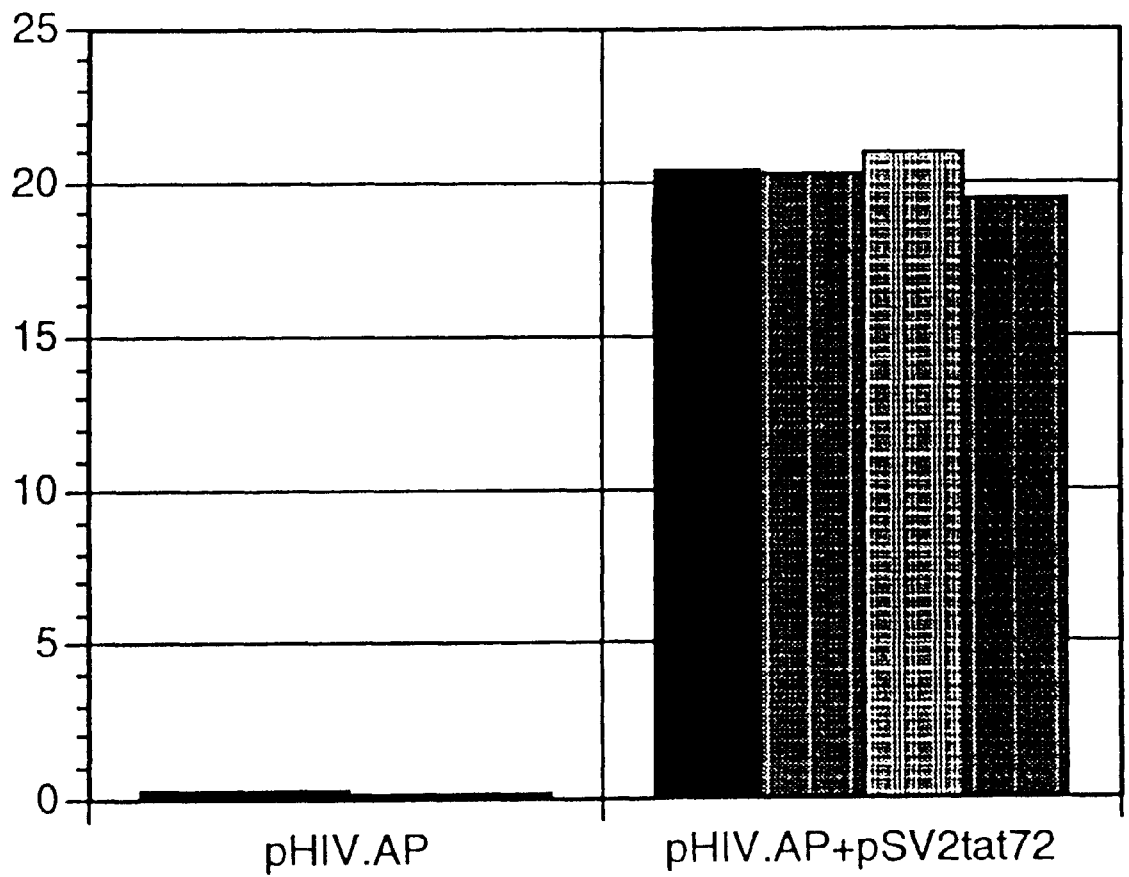
FIG. 1 shows AP reporter gene activity in 293-EBNA cells transiently transfected with pHIV.AP alone or in combination with pSVtat72. The expression level of AP increased by more than 50 fold in the presence of the tat expression vector, indicating transactivation of the HIV-LTR promoter by the 72 amino acid tat protein.

The invention provides methods for treating viral infection by preventing viral replication, viral gene expression and release of certain viral antigens in infected cells, comprising administering an effective amount of a compound that inhibits intracellular myrPA formation. The compound is a small organic molecule that can mimic binding to a complex of enzymes that mediate signal amplification at the cellular plasma membrane. Specifically the compound acts by preventing formation of myrPA species in cells stimulated to signal viral replication and proliferation. Therefore, by attacking a host cell signaling mechanism, the compounds do not have resistant viral strains due to rapid viral mutation that is common in antiviral agents that act against viral proteins and viral mechanisms. Moreover, we have found this intracellular signaling mechanism, several exemplary compounds that can be used to prevent further progression of viral diseases by inhibiting host cell viral replication, and have correlated the mechanism of drug action on a cellular basis with the disease to provide a definitive test for myrPA is stimulated host cells as a means for determining whether or not a candidate compound will be effective in preventing the further progression of viral-mediated diseases, such as AIDS or CMV diseases.

The invention further provides methods for preventing depletion of cells by cytokine-mediated apoptosis. Lymphocytes depleted by indirect effects of HIV infection can cause a general depletion of immune function. Such an effect includes induction of inflammatory cytokines (e.g., IL-1 and TNF) by HIV and by extracellular effects of HIV proteins, such as tat. Compounds, such as lisofylline and other compounds that inhibit intracellular accumulation of myrPA in stimulated cells (e.g., CT2576 and CT3556) interfere with PA pathways and thereby prevent lymphocyte depletion in HIV seropositive individuals.

The term "treating" in its various grammatical forms in relation to the present invention refers to preventing, curing, reversing, attenuating, alleviating, minimizing, suppressing or halting the deleterious effects of a disease state, disease progression, disease causitive agent (e.g., viruses) or other abnormal condition. Specific treatment effects include inhibition of the pathway that forms myrPA, inhibition of viral replication, viral gene expression, viral antigen release and other indicia of therapeutic activity discloses herein. An "effective amount" of a compound in an inventive method is the amount of compound necessary to prevent, cure, reverse, attenuate, alleviate, minimize, suppress or halt the deleterious effects of a disease state, disease progression, disease causitive agent (e.g., viruses) or other abnormal condition. An "effective amount" includes the dosage sufficient to inhibit of the pathway that forms myrPA, inhibit viral replication, viral gene expression, viral antigen release and other markers of therapeutic activity discloses herein. Specific forumulations and dosages are discussed below. Other formulations and dosages will become apparent to the skilled artisan in view of the teaching contained herein.

MyrPA Assay

This procedure begins with those cells that would be normally infected with a virus, such as a retrovirus. However, it is not necessary to utilize a cell line containing a retroviral genome, such as U1 cells. In view of the necessity to utilize containment facilities when using an infected cell line, it is preferable to utilize a macrophage cell line that is not infected. Examples of appropriate macrophage cell lines include, U937, THP1, U1, and P288s (available from standard sources, such as ATCC). The cells are stimulated with a stimulant with or without a candidate drug. Examples of stimulants include 3–5% serum, such as fetal calf serum, or tumor necrosis factor (TNF) (e.g., 20 ng/ml) both of which are standard laboratory reagents. After a time course (within 5 minutes, preferably within 1 minute), the cells are immersed in ice cold methanol to stop any cellular signaling reactions.

Figure 22:
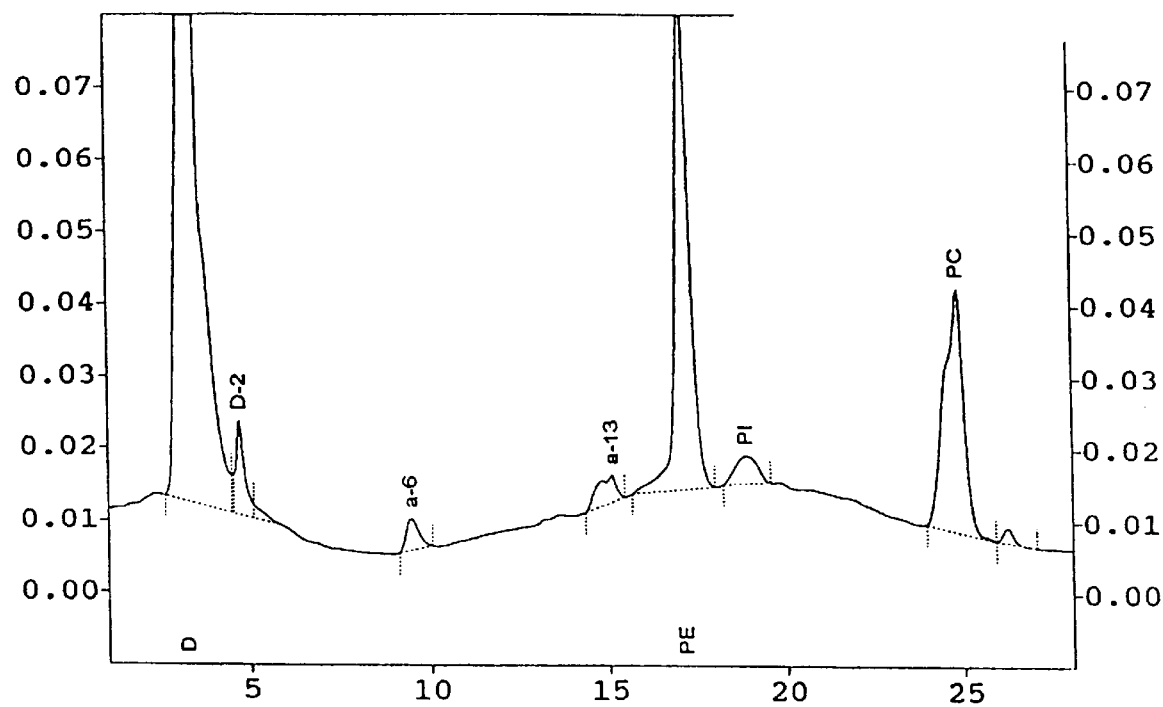
FIG. 22 shows an HPLC profile with the PA peak marked in stimulated but not treated cells.

One must first quantitatively and qualitatively separate PAs from the other lipids found in serum by a chemical extraction of lipids and high performance liquid chromatography (HPLC) to separate and detect PAs. Chemical extraction can be accomplished, for example, by the method of Bligh et al. (*Canadian J. Biochem. Physiol.* 37:911–917, 1959) or that of Folch et al. (*J. Biol. Chem.* 226:497–509, 1957). Briefly, the method of Bligh et al. involves an organic extraction of lipids from biological tissue homogenates or fluids. One volume of sample and three volumes of methanol:chloroform (2:1) are vigorously shaken for 2 min. One volume of chloroform is added and then shaken vigorously for 30 sec. One volume of water is added and then shaken vigorously for 30 sec. The mixture is filtered and the upper aqueous layer is discarded. The lower organic layer contains a mixture of lipid classes. The method of Folch et al.

involves the extraction of lipids from biological tissue homogenates or body fluids. One volume of sample plus 20 volumes of chloroform:methanol (2:1) are vigorously shaken for 2 min. The mixture is filtered and an amount of 0.1 N KCl equal to 20% of the extraction mixture volume is added and the mixture is shaken vigorously for 2 min. The aqueous and organic phases are allowed to separate. The upper aqueous layer is discarded. The lower organic layer contains a mixture of lipid classes. Free fatty acids and neutral lipids can be separated from phospholipids by normal phase high performance liquid chromatography (HPLC) by modifying the method of Van Kessel et al. (*Biochim et Biophys Acta* 486:524–530, 1977). This method involves separation of lipids into their major classes by normal phase (silica) high performance liquid chromatography (HPLC). A 5 micron, 25 cm×0.45 cm silica HPLC column is connected to a binary solvent delivery system followed with a UV detector. The lipid sample is injected on the column and a solvent gradient is run at 1.0 ml/min. The solvent gradient is hexane:isopropanol:water in the proportions 3:4:0.75 run isocratically for 3 min, then ramped to hexane:isopropanol:water in the proportions 3:4:1.4 in 15 min, then run isocratically at the same proportions for 15 min. Detection is at 206 nm. The PAs run at about 6–8 min when run at 1 ml/min when run in hexane:isopropanol (3:4) according to the HPLC peaks shown in FIG. 22 wherein the "PA peak" is listed as "D-2".

Once the PA peak is identified and isolated, it is subject to general alkaline hydrolysis or another method to isolate the FFAs (free fatty acids) from the PA species. This assay is based upon identifying myrPA species in particular such that the identity of the acyl side chains of PA species in stimulated cells is critical for determining if a candidate compound is effective for inhibiting host cell signaling in infected cells to inhibit viral replication and prevent further progression of viral diseases. The FFAs are isolated after hydrolysis.

Figure 23:
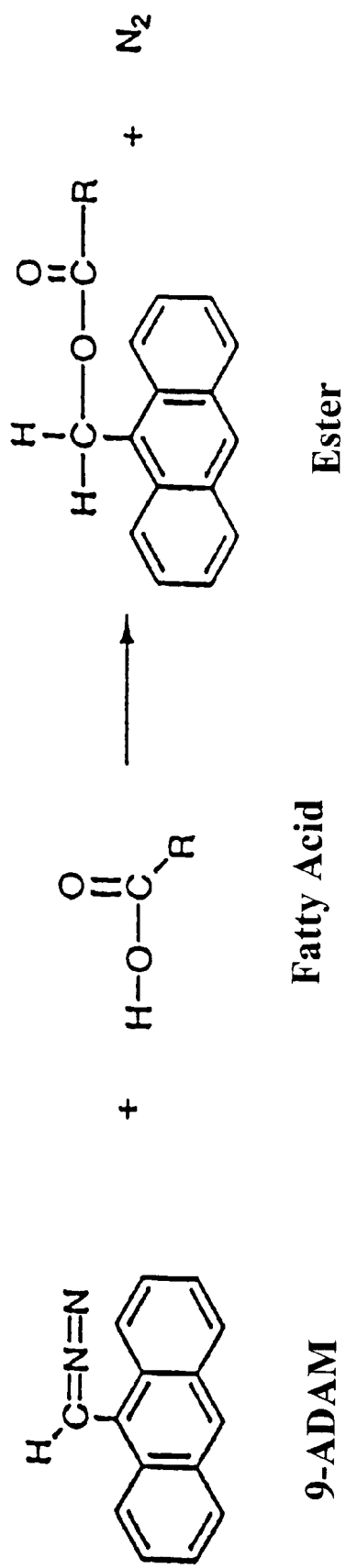
FIG. 23 illustrates the chemistry of a reaction to derivatize FFAs (free fatty acids) with 9-ADAM.

The isolated FFAs are derivatized into fatty acid derivatives of 9-anthroyl diazomethane (9-ADAM), which absorbs light at 254 nm and fluoresces with emission at 410 nm. FFA derivatives were prepared essentially according to the method described in Nakaya et al. (*Bull. Chem. Soc. Japan* 40:691–692, 1967, and Yoshida et al., *Analytical Biochem.* 173:70–74, 1988). The derivatization is based on the reaction shown in FIG. 23. Briefly, 9-anthraldehyde hydrazone for 9-anthroyl diazomethane derivatization was synthesized from 9-anthraldehyde and hydrazine monohydrate as follows: (a) 8.8 g 9-anthraldehyde (Aldrich Milwaukee, Wis.) was dissolved in 150 mL absolute ethanol and 8 mL hydrazine monohydrate (Aldrich Milwaukee, Wis.) was added dropwise with continual stirring. (b) The mixture cleared as hydrazine was added then turned opaque as the last drops were added. (c) The reaction was stirred at room temperature for 3 hr, then was filtered (Whatman #1 filter paper, Whatman Int. Maidstone UK) and dried. (d) The product was recrystalized twice with absolute ethanol. (e) The yield was 3.1 g of needle-like crystals.

Figure 24:
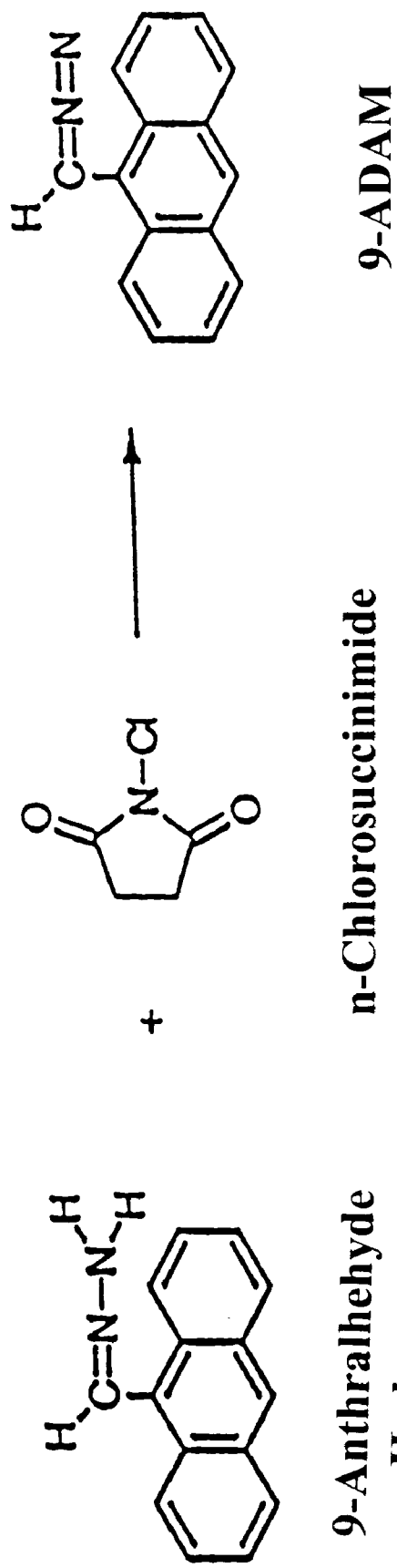
FIG. 24 illustrates the chemistry of a reaction to make a 9-ADAM derivatizing reagent.

The following solutions were made in ethyl acetate: 9-anthraldehyde hydrazone (0.0276 $\mu$M, 0.0304 g/5 mL), Quinuclidine (0.2760 M, 0.1534 g/5 mL (oxidizing reagent)), and N-chlorosuccinimide (0.0276M, 0.0184 g/5 mL (catalyst)). Equal volumes of these solutions were mixed to react at room temperature for 30 min. The resulting 9-anthryl diazomethane (9-ADAM) was unstable and was made fresh daily. This reaction is shown in FIG. 24.

The derivatizating reaction was carried out by diluting 50 $\mu$L of each FFA standard to 200 $\mu$L with methanol. FFA standards (1.0 mg/mL) were made up in methanol using: Heptadecanoic acid 17:0 (Aldrich Chemical Milwaukee, Wis.); Arachidonic acid 20:4 (Matreya, Inc., Pleasant Gap, Pa.); Linoleic acid 18:2 (Matreya, Inc., Pleasant Gap, Pa.); Linolenic acid 18:3 (Matreya, Inc., Pleasant Gap, Pa.); Palmitic acid 16:0 (Matreya, Inc., Pleasant Gap, Pa.); Oleic acid 18:1 (Matreya, Inc., Pleasant Gap, Pa.); Stearic acid 18:0 (Matreya, Inc., Pleasant Gap, Pa.); Myristic acid 14:0 (Matreya, Inc., Pleasant Gap, Pa.); Lauric acid 12:0 (Matreya, Inc., Pleasant Gap, Pa.); Arachidic acid 20:0 (Matreya, Inc., Pleasant Gap, Pa.); and n-Docosanoic acid 22:0 (Matreya, Inc., Pleasant Gap, Pa.). Derivatizing solution (200 $\mu$L) was added. The mixture was reacted for 1 hr at room temperature to form each derivatized standard. 20 $\mu$L was injected into an HPLC and run by a reverse phase method described below.

A reverse phase HPLC procedure used to separate and quantitate the derivatized anthroyl FFAs. A reverse phase "C8" column (4.6 cm×25 cm, 5 micron Spherisorb® C8, Alltech Associates, Inc. Deerfield, Ill.) separated the saturated FFAs. A 3 micron, 15 cm "C18" column was connected to the HPLC followed by a 5 micron, 25 cm "C8" column. The high performance liquid chromatograph was a model 517 from Gilson Medical Electronics, Inc., Middleton, Wis. Two detectors were connected in tandem. The first was Model UVIS 200 from Linear Instruments, Reno, Nev. The second was Model 121 Fluorometer from Gilson Medical Electronics.

Table 2 below shows the chromatographic conditions used.

TABLE 2

| UV Detection: | 254 nm |
|---|---|
| Fluorescent Detection: | |
| Excitation: | 305–395 nm bandpass filter |
| Emission: | 430–470 nm bandpass filter |
| Buffer A: | 70% Acetonitrile:30% $H_2O$ |
| Buffer B: | 100% Acetonitrile |
| Flow: | 1.0 mL per min |
| Gradient: | 40% B for 2 min |
| | from 40% to 45% B in 18 min |
| | from 45% to 54% B in 10 min |
| | from 54% to 70% B in 5 min |
| | from 70% to 94% B in 19 min |
| | from 94% to 99% B in 1 min |
| | 99% B for 29 min |
| | from 99% to 40% B in 1 min |
| | 40% B for 5 min |

The foregoing method was used to correlate the intracellular mechanisms of cell signaling inhibition of the exemplary compounds with the predictive antiviral data in general and the ability to prevent HIV replication in particular. Therefore, the invention provides methods for preventing the progression of viral diseases by inhibiting a host cell viral replication mechanism comprising administering an effective amount of a compound that can inhibit myrPA formation in stimulated cells.

Mechanism of Action

The compounds described herein exert their antiviral activity by inhibiting one or a plurality of enzymes or an enzyme complex, resulting in a diminution of host (or infected) cell myrPA formation in response to an inflammatory stimulus (e.g., TNF or IL-1). Therefore, the inventive compounds describe a genus of compounds that share a common mechanism of action, on a cellular level, that results in decreased intracellular signaling within a virally-infected cell, that does not transmit an inflammatory signal that would otherwise (in the absence of drug) signal an infected cell to begin the process of viral replication, gene expression, assembly and virion shedding. This cellular and biochemical mechanism of action, as illustrated by cells infected by the HIV virus as described herein, provides evidence for a general antiviral activity of the genus of compounds described herein, or other compounds that exert a similar mechanism of action (that is, prevention of infected host cell PA accumulation in response to an inflammatory stimulus) by virtue of the ability of the drug to prevent normal viral replication and gene expression within an infected host cell. These compounds further prevent the release of certain viral antigens from the host cell.

Examples of other viruses that replicate and demonstrate increased gene expression in an infected host cell in response to inflammatory stimuli (usually mediated by the cytokines TNF or IL-1) include, for example, cytomegalovirus (CMV), herpes family of viruses, including herpes simplex virus (HSV) 1, 2 and 6, hepatitis A, B, C and D, HIV 1 and 2, Epstein Barr virus (EBV), human T cell leukemia virus (HTLV), human papiloma virus, influenza, parainfluenza, respiratory syncytial virus, all adenoviruses, and rhinoviruses. Therefore, the inventive treatment method results in prevention of progression of a viral disease, comprising administering an effective amount of a compound that can reduce intracellular myrPA concentrations in response to an inflammatory stimulus. Examples of viral diseases include, for example, CMV retinitis, AIDS, systemic viral diseases affecting immunocompromised individuals (e.g., AIDS or transplant recipients), cold sores (HSV-1), genital herpes (HSV-2), hepatitis (A, B or C, or HSV-6), genital warts (human papiloma virus), infectious mononucleosis and some lymphomas (EBV), shingles (*Varicella zoster*), *pericarditis (coxsackie virus), influenza, and cold and flu (rhinoviruses and adenoviruses)*.

One notable feature of HIV-1 infection and many other viral infections (such as HSV) is its prolonged incubation period during which the virus is harbored in a quiescent state in (in the case of HIV-1) CD4 lymphocytes and mononuclear phagocytes. Often, there are inflammatory cofactors that can accelerate progression of the disease by upregulating expression of the virus, such as HIV-1, in chronically infected cells. One such cofactor for HIV-1 infection is human cytomegalovirus (HCMV), which is a cause of serious opportunistic infection in AIDS patients. It has been proposed that cytokines, particularly TNF, IL-6 and IL-1 play an important role in upregulating viral replication in infected cells (Clouse et al., *J. Immunol.* 143:470, 1989). Therefore, blocking intracellular signaling of such inflammatory cytokines can serve to ablate the inflammatory signal and inhibit the upregulating event that normally triggers viral replication and gene expression in infected cells.

The mammalian cell membrane associated enzyme lysophosphatidate acyl-CoA acyltransferase (LPAAT) catalyzes the transfer of acyl CoA from lysophosphatidic acid (lyso-PA) to phosphatidic acid (PA) species. Certain PA species function as lipid intermediates in cell activation and function directly as intracellular signaling molecules. PA is subsequently dephosphorylated to 1,2-sn diacylglycerol (DAG) via phosphatidate phosphohydrolase (PAH). The compounds that inhibit viral replication, gene expression and viral antigen release in infected cells also have decreased amounts of intracellular PA species that are formed in response to inflammatory cellular activation. For example, CT1501R (R-1(5-hydroxyhexyl)3,7-dimethylxanthine) or lisofylline (generic name) demonstrates antiviral activity by inhibiting HIV replication, gene expression and p24 release in infected monocytic cells stimulated to produce virions by TNF activation. CT1501R is also and inhibitor of LPAAT in vitro with competitive inhibition in a Lineweaver-Burke graph and an $IC_{50}$ for LPAAT inhibition in the range of 200 to 400 nM. Therefore, if PA derived from lyso-PA is an important intracellular signaling intermediate for TNF or IL-1 induced viral replication in virally-infected cells, then inhibitors of PA formation will act to prevent progression of viral diseases by blocking cell signaling to stimulate virion formation. The compounds illustrated herein that are shown to inhibit virion formation or block promoter activity also inhibit PA formation.

The invention provides methods for treating viral infections and diseases, comprising administering an effective amount of a compound that inhibits cellular accumulation of myrPA, thereby decreasing cellular accumulation of viral gene products. This invention further provides a specific method of treating and delaying or preventing the occurrence of AIDS, which comprises administering to an HIV seropositive human an effective amount of a compound, or a pharmaceutically acceptable salt or hydrate or solvate thereof, wherein said compound can block intracellular myrPA formation from lyso-PA.

The invention also provides methods of treating acquired immunodeficiency syndrome in HIV seropositive patients, comprising adminstering an effective amount of a compound that inhibits cellular accumulation of myrPA in stimulated moncytic cells. Another aspect of the instant invention provides methods of inhibiting the progression of HIV infection in an HIV seropositive patient, comprising administering an effective amount of a compound that inhibits cellular accumulation of myrPA in stimulated monocytic cells, thereby decreasing the accumulation of HIV gene products.

Preferably, the compound of the above methods is an amino alcohol-substituted or chiral primary or secondary alcohol-substituted heterocyclic compound wherein the heterocyclic moiety is a substituted or unsubstituted xanthine, a substituted or unsubstituted uracil or a substituted or unsubstituted thymine. An amino alcohol or chiral primary or secondary alcohol compound, or a pharmaceutically acceptable salt or hydrate or solvate thereof, can be administered to such human in a conventional dosage form prepared by combining the amino alcohol or chiral primary or secondary alcohol compound or a pharmaceutically acceptable salt or hydrate or solvate thereof, with a conventional pharmaceutically acceptable carrier or diluent according to known pharmaceutical formulation techniques. Moreover, the compound may be formulated into an opthalmic formulation for ocular administration to treat, for example, CMV retinitis. Topical formulations of compound are appropriate for the treatment of herpes types I and II and for papilloma virus.

Illustrative Compounds

The compound that can inhibit myristilated PA (myrPA) in either the sn-1 or sn-2 positions or both can be determined by following an assay procedure described herein. Preferably, the compound is a small organic molecule that can mimic binding to a complex of enzymes that mediate signal amplification. The compounds include resolved enantiomers and/or diastereomers, hydrates, salts, solvates and mixtures thereof, wherein the compounds having a straight or branched aliphatic hydrocarbon of the general formula:

$$(X)_j-R_4.$$

In this general formula j is an integer from one to three. $R_4$ is a terminal moiety comprising a substituted or unsubstituted, carbocyclic or heterocyclic moiety or open chain analogs thereof. When $R_4$ is a heterocyclic moiety, it consists essentially of one to three ring structures having 5–7 members each, a heteroatom, and a predominantly planar structure or essentially aromatic.

X of the general formula is a racemic mixture or R or S enantiomer of:

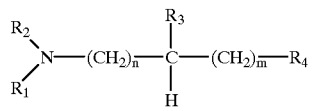

I wherein n is an integer from one to four and m is an integer from four to twenty. $R_1$ and $R_2$ are hydrogen, a straight or branched chain alkyl, alkenyl or alkynyl of up to twenty carbon atoms in length or —$(CH_2)_w R_5$. Optionally, $R_1$ and $R_2$ may jointly form a substituted or unsubstituted, saturated or unsaturated heterocycle having from four to eight carbon atoms. $R_3$ is hydrogen, a hydroxy group, a $C_{1-3}$ straight or branched alkyl, or a $C_{1-3}$ alkoxy.

$R_5$ is an hydroxyl, halo, $C_{1-8}$ alkoxyl group or a substituted or unsubstituted carbocycle or heterocycle. $R_5$ can be a substituted or unsubstituted aryl group wherein the substituted aryl group is mono, di or tri substituted with hydroxy, chloro, fluoro, bromo, or alkoxy (C1-6) substituents, or

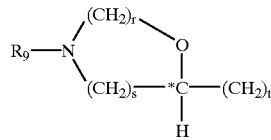

$R_9$ is a hydrogen or a straight or branched chain alkane or alkene of up to eight carbon atoms in length, —$(CH_2)_m R_5$. Alternatively, $R_9$ forms a cyclo saturated or unsaturated aromatic ring or substituted aromatic ring having from four to eight carbon atoms and including the nitrogen atom within the ring. r and s are independently integers from one to four, the sum (r+s) is not greater than five. One or more carbon atoms in $(CH_2)_r$ or $(CH_2)_s$ may be substituted by a keto or hydroxy group, t is an integer from one to fourteen, and $R_5$ is a substituted or unsubstituted aryl group wherein the substituted aryl group is mono, di or tri substituted with hydroxy, chloro, fluoro, bromo, or alkoxy (C1-6) substituents.

Alternatively, X is independently a resolved enantiomer ω-1 secondary alcohol-substituted alkyl ($C_{5-8}$) substantially free of the other enantiomer, or X is a branched —$(CH_2)$a-$CHR_6$—$(CH_2)$b-$R_7$, wherein a is an integer from about 4 to about 12, b is an integer from 0 to 4, $R_6$ is an enantiomer (R or S) or racemic mixture ($C_{1-6}$) alkyl or alkenyl, and $R_7$ is a hydroxy, keto, cyano, chloro, iodo, flouro, or chloro group.

Preferred compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+a number of carbon atoms in the linking carbon chain being less than six.

In the compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, heterocyclic moiety, wherein the heterocyclic moiety consists essentially of one to three ring structures having 5–7 members each, a heteroatom, and a predominantly planar structure or essentially aromatic. However, if $R_4$ is phthalimide, m of formula I is not less than five.

The compounds may include resolved enantiomers and/or diastereomers, hydrates, salts, solvates and mixtures thereof that have a straight or branched aliphatic hydrocarbon structure of formula II:

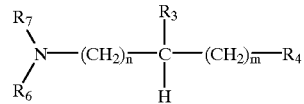

II

In the above formula II, n, m, $R_3$, and $R_4$ are defined as provided in formula I above. $R_6$ and $R_7$ are hydrogen, a straight or branched chain alkane, alkene or alkyne of up to twenty carbon atoms in length, or —$(CH_2)_x R_8$, at least one of $R_6$ or $R_7$ being —$(CH_2)_x R_8$. In formula II, x is an integer from zero to fourteen and $R_8$ is a moiety having a general structure as provided in formula III:

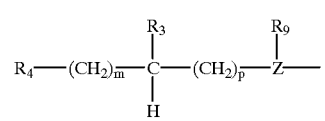

III

In formula III above, m, $R_3$, and $R_4$ are defined as provided in formula I above. Z is N or CH and p is an integer from zero to four. $R_9$ is H or a straight or branched chain alkane, alkene or alkyne of up to twenty carbon atoms in length.

For example, $R_4$ may be selected from the group consisting of substituted or unsubstituted acridinyl; acridonyl; alkylpyridinyl; anthraquinonyl; ascorbyl; azaazulenyl; azabenzanthracenyl; azabenzanthrenyl; azabenzophenanthrenyl; azachrysenyl; azacyclazinyl; azaindolyl; azanaphthacenyl; azanaphthalenyl; azapyrenyl; azatriphenylenyl; azepinyl; azinoindolyl; azinopyrrolyl; benzacridinyl; benzazapinyl; benzamidyl; benzofuryl; benzonaphthyridinyl; benzopyranonyl; benzopyranyl; benzopyronyl; benzoquinolinyl; benzoquinolizinyl; benzothiepinyl; benzothiophenyl; benzylisoquinolinyl; biotinyl; bipyridinyl; butenolidyl; butyrolactonyl; caprolactamyl; carbazolyl; carbolinyl; catechinyl; chromenopyronyl; chromonopyranyl; coumarinyl; coumaronyl; decahydroquinolinyl; decahydroquinolonyl; diazaanthracenyl; diazaphenanthrenyl; dibenzazepinyl; dibenzofuranyl; dibenzothiophenyl; dichromylenyl; dihydrofuranyl; dihydroisocoumarinyl; dihydroisoquinolinyl; dihydropyranyl; dihydropyridinyl; dihydropyridonyl; dihydropyronyl; dihydrothiopyranyl; diprylenyl; dioxanthylenyl; enantholactamyl; flavanyl; flavonyl; fluoranyl; fluorescienyl; flutarimidyl; furandionyl; furanochromanyl; furanonyl; furanoquinolinyl; furanyl; furopyranyl; furopyronyl; ;glutarimidyl; heteroazulenyl; hexahydropyrazinoisoquinolinyl; homopthalamidyl; hydrofuranyl; hydrofurnanonyl; hydroindolyl; hydropyranyl; hydropyridinyl; hydropyrrolyl; hydroquinolinyl; hydrothiochromenyl; hydrothiophenyl; imidizoamidyl; indolizidinyl; indolizinyl; indolonyl; isatinyl; isatogenyl; isobenzofurandionyl; isobenzofuranyl; isochromanyl; isoflavonyl; isoindolinyl; isoindolobenzazepinyl; isoindolyl; isoquinolinyl; isoquinuclidinyl; lactamyl; lactonyl; maleimidyl; monoazabenzonaphthenyl; naphthalenyl; naphthimidazopyridinedionyl; naphthindolizinedionyl; naphthodihydropyranyl; naphthofuranyl; naphthothiophenyl; naphthyridinyl; oxepinyl; oxindolyl; oxolenyl; perhydroazolopyridinyl; perhydroindolyl; phenanthraquinonyl; phenanthridinyl; phenanthrolinyl; phthalideisoquinolinyl; phthalimidyl; phthalonyl; piperidinyl; piperidonyl; prolinyl; pyradinyl; pyranoazinyl; pyranoazolyl; pyranopyrandionyl; pyranopyridinyl; pyranoquinolinyl; pyranopyradinyl; pyranyl; pyrazolopyridinyl; pyridinethionyl; pyridinonaphthalenyl; pyridinopyridinyl; pyridinyl; pyridocolinyl; pyridoindolyl; pyridopyridinyl; pyridopyrimidinyl; pyridopyrrolyl; pyridoquinolinyl; pyronyl; pyrrocolinyl; pyrrolamidinyl; pyrrolidinyl; pyrrolizidinyl; pyrrolizinyl; pyrrolodiazinyl; pyrrolonyl; pyrrolopyrimidinyl; pyrroloquinolonyl; pyrrolyl; quinacridonyl; quinolinyl; quinolizidinyl; quinolizinyl; quinolonyl; quinuclidinyl; rhodaminyl; spirocoumaranyl; succinimidyl; sulfolanyl; sulfolenyl; tetrahydrofuranyl; tetrahydroisoquinolinyl; tetrahydropyranyl; tetrahydropyridinyl; tetrahydrothiapyranyl; tetrahydrothiophenyl; tetrahydrothiopyranonyl; tetrahydrothiopyranyl; tetronyl; thiabenzenyl; thiachromanyl; thiadecalinyl; thianaphthenyl; thiapyranyl; thiapyronyl; thiazolopyridinyl; thienopryidinyl; thienopyrrolyl; thienothiophenyl; thiepinyl; thiochromenyl; thiocoumarinyl; thiophenyl; thiopyranyl; triazaanthracenyl; triazinoindolyl; triazolopyridinyl; tropanyl; xanthenyl; xanthonyl, xanthydrolyl; adeninyl; alloxanyl; alloxazinyl; anthranilyl; azabenzanthrenyl; azabenzonaphthenyl; azanaphthacenyl; azaphenoxazinyl; azapurinyl; azinyl; azoloazinyl; azolyl; barbituric acid; benzazinyl; benzimidazolethionyl; benzimidazolonyl; benzimidazolyl; benzisothiazolyl; benzisoxazolyl; benzocinnolinyl; benzodiazocinyl; benzodioxanyl; benzodioxolanyl; benzodioxolyl; benzopyridazinyl; benzothiazepinyl; benzothiazinyl; benzothiazolyl; benzoxazinyl; benzoxazolinonyl; benzoxazolyl; cinnolinyl; depsidinyl; diazaphenanthrenyl; diazepinyl; diazinyl; dibenzoxazepinyl; dihydrobenzimidazolyl; dihydrobenzothiazinyl; dihydrooxazolyl; dihydropyridazinyl; dihydropyrimidinyl; dihydrothiazinyl; dioxanyl; dioxenyl; dioxepinyl; dioxinonyl; dioxolanyl; dioxolonyl; dioxopiperazinyl; dipyrimidopyrazinyl; dithiolanyl; dithiolenyl; dithiolyl; flavinyl; furopyrimidinyl; glycocyamidinyl; guaninyl; hexahydropyrazinoisoquinolinyl; hexahydropyridazinyl; hydantoinyl; hydroimidazolyl; hydropyrazinyl; hydropyrazolyl; hydropyridazinyl; hydropyrimidinyl; imidazolinyl; imidazolyl; imidazoquinazolinyl; imidazothiazolyl; indazolebenzopyrazolyl; indoxazenyl; inosinyl; isoalloxazinyl; isothiazolyl; isoxazolidinyl; isoxazolinonyl; isoxazolinyl; isoxazolonyl; isoxazolyl; lumazinyl; methylthyminyl; methyluracilyl; morpholinyl; naphthimidazolyl; oroticyl; oxathianyl; oxathiolanyl; oxazinonyl; oxazolidinonyl; oxazolidinyl; oxazolidonyl; oxazolinonyl; oxazolinyl; oxazolonyl; oxazolopyrimidinyl; oxazolyl; perhydrocinnolinyl; perhydropyrroloazinyl; perhydropyrrolooxazinyl; perhydropyrrolothiazinyl; perhydrothiazinonyl; perimidinyl; phenazinyl; phenothiazinyl; phenoxathiinyl; phenoxazinyl; phenoxazonyl; phthalazinyl; piperazindionyl; piperazinodionyl; polyquinoxalinyl; pteridinyl; pterinyl; purinyl; pyrazinyl; pyrazolidinyl; pyrazolidonyl; pyrazolinonyl; pyrazolinyl; pyrazolobenzodiazepinyl; pyrazolonyl; pyrazolopyridinyl; pyrazolopyrimidinyl; pyrazolotriazinyl; pyrazolyl; pyridazinyl; pyridazonyl; pyridopyrazinyl; pyridopyrimidinyl; pyrimidinethionyl; pyrimidinyl; pyrimidionyl; pyrimidoazepinyl; pyrimidopteridinyl; pyrrolobenzodiazepinyl; pyrrolodiazinyl; pyrrolopyrimidinyl; quinazolinonyl; quinazolinyl; quinolinyl; quinoxalinyl; sultamyl; sultinyl; sultonyl; tetrahydrooxazolyl; tetrahydropyrazinyl; tetrahydropyridazinyl; tetrahydroquinoxalinyl; tetrahydrothiazolyl; thiazepinyl; thiazinyl; thiazolidinonyl; thiazolidinyl; thiazolinonyl; thiazolinyl; thiazolobenzimidazolyl; thiazolyl; thienopyrimidinyl; thiazolidinonyl; thyminyl; triazolopyrimidinyl; uracilyl; xanthinyl; xylitolyl, azabenzonaphthenyl; benzofuroxanyl; benzothiadiazinyl; benzotriazepinonyl; benzotriazolyl; benzoxadizinyl; dioxadiazinyl; dithiadazolyl; dithiazolyl; furazanyl; furoxanyl; hydrotriazolyl; hydroxytrizinyl; oxadiazinyl; oxadiazolyl; oxathiazinonyl; oxatriazolyl; pentazinyl; pentazolyl; petrazinyl; polyoxadiazolyl; sydononyl; tetraoxanyl; tetrazepinyl; tetrazinyl; tetrazolyl; thiadiazinyl; thiadiazolinyl; thiadiazolyl; thiadioxazinyl; thiatriazinyl; thiatriazolyl; thiatriazolyl; triazepinyl; triazinoindolyl; triazinyl; triazolinedionyl; triazolinyl; triazolyl; trioxanyl; triphenodioxazinyl; triphenodithiazinyl; trithiadiazepinyl; trithianyl; trixolanyl.

In these compounds, the most preferred ring systems ($R_4$) include, for example, dimethylxanthinyl, methylxanthinyl, phthalimidyl, homophthalimidyl, methylbenzoyleneureayl, quinazolinonyl, octylcarboxamidobenzenyl, methylbenzamidyl, methyldioxotetrahydropteridinyl, glutarimidyl, piperidonyl, succinimidyl, dimethoxybenzenyl, methyldihydrouracilyl, methyluracilyl, methylthyminyl, piperidinyl, dihydroxybenzenyl, methylpurinyl, 1,3-cyclohexanedione, 1,3-cyclopentanedione, 1,3-dihydroxynaphthalene, 1-methyllumazine, methylbarbituric acid, 3,3-dimethylflutarimide, 2-hydroxypyridine, methyldihydroxypyrazolopyrimidine, 1,3-dimethyldihydroxypyrazolo[4,3-d]pyrimidine, methylpyrrolopyrimidine, 1-methylpyrrolo [2,3-d] pyrimidine, 2-pyrrole amides, 3-pyrrole amides, 1,2,3,4-tetrahydroisoquinolone, 1-methyl-2,4(1H,3H)-quinazolinedione (1-methylbenzoyleneurea, quinazolin-4(3H)-one, alkyl-substituted ($C_{1-6}$) thymine, methylthymine, alkyl-substituted ($C_{1-6}$) uracil, 6-aminouracil, 1-methyl-5,6-dihydrouracil, 1-methyluracil, 5- and/or 6-position substituted uracils, 1,7-dimethylxanthine, 3,7-dimethylxanthine, 3-methylxanthine, 3-methyl-7-methylpivaloylxanthine, 8-amino-3-methylxanthine, 7-methylhypoxanthine, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, pteridine, 1-methyl-2,4(1H,3H)-quinazolinedione (1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4,3-d] pyrimidine, 5-substituted uracils, 6-substituted uracils, 1-methylpyrrolo [2,3-d]pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, quinazolin-4(3H)-one or derivatives thereof.

Preferred and exemplary compounds are used throughout the specification and are designated by CT# according to Table 1 below.

TABLE 1

| | |
|---|---|
| CT1501R | R-1-(5-hydroxyhexyl)-3,7-dimethylxanthine |
| CT1115 | N-(11-octylamino-10-hydroxyundecyl)homophthalimide |
| CT1416 | N-(11-octylamino-10-hydroxyundecyl)-3-methylxanthine |
| CT1620 | N-(11-octylamino-10-hydroxyundecyl)-2-piperdone |
| CT1827 | 3-(11-octylamino-10-hydroxyundecyl)-1-methyluracil |
| CT1829 | 3-(11-octylamino-10-hydroxyundecyl)-1-methyldihydrouracil |
| CT2571 | 1-(9-decylamino-8-hydroxynonyl)-3,7-dimethylxanthine |
| CT2573 | 1-(9-dodecylamino-8-hydroxynonyl)-3,7-dimethylxanthine |
| CT2575 | 1-(11-hexylamino-8-hydroxyundecyl)-3,7-dimethylxanthine |

TABLE 1-continued

| | |
|---|---|
| CT3528 | N-(11-phenylamino-10-hydroxundecyl)-3,7-dimethylxanthine |
| CT2576 | 1-(11-octylamino-10-hydroxyundecyl)-3,7-dimethylxanthine |
| CT3556 | 1-(11-N-octylaminoundecyl)-3,7-dimethylxanthine |
| CT3537 | 1-[11-(N-octylacetamido)-10-acetoxyundecyl]-3,7-dimethylxanthine |
| CT3534 | 1-(9-(2-hydroxydecyl-1-amino)nonyl)-3,7-dimethylxanthine |

Antiviral Assays

An assay for measuring the anti-viral activity of the compounds involves testing the abilities of the compounds to inhibit gene expression directed by specific viral promoters in cell lines. Specifically, a plasmid construct, pCMV.AP, using the human cytomegalovirus (CMV) enhancer and promoter to direct the expression of the secreted human placental alkaline phosphatase reporter gene were transformed into a tumor cell line (e.g., 293-EBNA cells). The cultured cells were treated with various concentrations of the compounds. The expression of the alkaline phosphatase (AP) reporter gene in the individual cultures can then be measured by following the change in absorbance at A405 of the cell conditioned media in the presence of a suitable substrate (e.g., ortho-nitrophenol phosphate) (Berger et al., Gene 66:1,1988).

The construction of expression vectors for secreted placental alkaline phosphatase (sPAP) was performed by obtaining a mammalian episomal expression vector pBL3, derived from the plasmids pMEP4 and pCEP4 (Invitrogen Corp). Specifically, a 600 bp Spe I—Kpn I fragment spanning the CMV promoter from pCEP4 and a 9500 bp Xba I—Kpn I vector fragment from pMEP4 were isolated and ligated together to form pBL3. Full length sPAP cDNA was amplified by PCR using the plasmid pGEM4Z/SEAP (ATCC) as template with primers 5'-GGATCCTCTAGACATGCTGGGGCCCTGCA-3' (SEQ ID NO. 1) and 5'-GGATCCGTCGACGTTAACCCGGGTGCGCG-3' (SEQ ID NO. 2). The PCR product was then digested with Xba I and Sal I and inserted between the Nhe I site and the Xho I site within the multiple cloning region of pBL3. The resulting plasmid was designated as PCMV.AP.

The plasmid construct, pHIV.AP, using the human immunodeficiency virus (HIV) long terminal repeat (LTR) promoter (derived from pU3R-III CAT, Sodroski et al., Science 227:171, 1985) to direct the expression of the sPAP reporter gene, was made by replacing the CMV promoter region from pCMV.AP with the HIV-LTR promoter. PHIV.AP was co-transfected with pSV2tat72, an expression vector for the 72 amino acids tat protein from HIV (Frankel and Pabo, Cell 55:1189–1193, 1988), into 293-EBNA cells (Invitrogen). The cultured cells were treated with various concentrations of the compounds. The expression of the alkaline phosphatase (AP) reporter gene in the individual cultures was measured by following change in absorbance at 405 nm of the cell conditioned media in the presence of a suitable substrate (e.g., ortho-nitrophenol phosphate) (Berger et al., Gene 66:1–10, 1988).

Another assay examined the effect of compounds on chronically HIV-1 infected U1 cells. A relatively high density of U1 cells at $10^4$ cells/well were incubated in the absence or presence of compounds for 4 days. HIV-1 p24 antigen expression in the culture media was measured by using a ELISA kit (Abbott). Alternatively, U1 cells were plated at a relatively low density of $2 \times 10^3$ cell/well plus or minus TNF at 20 pg/ml and plus or minus compounds. The expression of HIV-1 p24 antigen in culture media was measured by ELISA four days later.

Several compounds have been identified that inhibit CMV promoter driven expression with minimal cytotoxic effects. These compounds, (e.g., CT2575, CT1827 and CT1829) were also able to inhibit HIV promoter driven expression with minimal cytotoxic effects. As CMV is known to be a cause of serious opportunistic infection in AIDS patients (Schooley, Rev. Infect. Dis. 12 (Suppl.):811,1990) as well as a cofactor for HIV expression in infected cells (Peterson et al., J. Clin. Invest. 89:574,1992), compounds that are capable of inhibiting both the HIV promoter and the CMV promoter are of therapeutic interest in AIDS treatment. Moreover, the mechanism of action of the compounds in inhibiting both HIV and CMV viral replication, coupled with their biochemical mechanism of action in inhibiting specific intacellular signaling pathways, provides a conclusion that not only the illustrated compounds, but other compounds that have similar mechanisms of action in inhibiting intracellular signaling through myrPA, are therapeutically useful to treat or prevent progression of a large number of viral infections.

We set up a cell-based system with a cell line cotransfected with an expression plasmid using HIV-1-LTR promoter to direct synthesis of AP reporter gene and an expression plasmid to direct synthesis of the first 72 amino acids of tat protein. Plasmid pREP7 (Invitrogen) was converted to pREP7b by deleting 2,040 bp EBNA-1 coding region and by replacing the pBR322 origin of replication (ori) with the pBluescript KS (Stratagene) ori region. The cDNA for secreted placental alkaline phosphatase (AP) was generated by PCR with the primers (5'-GGATCCTCTAGACATGCTGGGGCCCTGCATGC-3') (SEQ ID NO. 3) and (5'-AAGCTTGTCGACGTTAACCCGGGTGCGCGGC-3') (SEQ ID NO. 4)using the plasmid pGEM-4Z/PLAP489 (American Type Culture Collection) as the template. The 2,000 bp Xba I-Sal I fragment obtained was ligated into a Nhe I/Xho I vector derived from pREP7b to generate the plasmid pREP7b.AP. The 44 bp Xba I-Bgl II fragment from plasmid pMEP4 (Invitrogen) and the 36 bp BamH I-Kpn I fragment from pREP7 were ligated into the Xba I-Kpn I vector fragment from pREP7b.AP to generate the plasmid pMCS.AP. The 720 bp Xho I-Hind III fragment encoding the HIV-LTR promoter from the plasmid pU3R-III-CAT (Sodroski et al., Science 227:171–173, 1985) was ligated into the Xho I-Hind III vector fragment of PMCS.AP to generate the plasmid pHIV.AP. The CMV promoter was derived from the 600 bp Spe I-Asp718 I fragment from pCEP4 (Invitrogen). The 360 bp SV40 early promoter fragments were produced from pSV2tat72 (Frankel et al., Cell 55:1189–1193, 1988) by PCR using the primers (5'-GAGGCAGCTCTAGAATGTGTGTCAGTTA-3') (SEQ ID NO. 5) and (5'-GTCTACCGGTACCAAGCTTTTTGCAA-3') (SEQ ID NO. 6). The 480 bp phosphoglycerate kinase (PGK) promoter fragment was amplified from human placental genomic DNA (Promega, Madison, Wis.) based on published sequence (Pfeifer et al., Science 246:810–813, 1990) using the primers (5'-GGAATTCTAGAGGTTGGGGTTGCGCCTT-3') (SEQ ID NO. 7) and (5'-AACGAGGGAGCCGGGTACCGACGTGCGC-3') (SEQ ID NO. 8). The above fragments were ligated into the Xba I-Asp718 I vector fragment of pHIV.AP to generate pHIV2.AP, pHIV3.AP, pCMV.AP, pSVE.AP and PPGK.AP respectively. The tat-expression plasmid directed by HIV-LTR promoter, pHIV.tat, was generated by inserting the 400 bp EcoRV-HindIII fragment from pHIV.AP into the PvuII-HindIII vector fragment from pSV2tat72 (Frankel et al., Cell 55:1189–1193, 1988).

NFκB binding activity in nuclear extracts (Dignam et al., *Nucleic Acids Res.* 11:1475–1489, 1983) of cells was measured by electrophoretic mobility-shift assay (EMSA) (Carthew et al., *Cell* 43:439–448, 1985) using 5'-labeled double-stranded synthetic DNA with two NF-κB motifs. Northern blot analysis was performed with total RNA run on 1% agarose/formaldehyde gel and probed with $^{32}$P-labeled cDNA of AP and glyceraldehyde-3-phosphate dehydrogenase (G3PDH).

Transient transfections with various expression plasmids were performed on a human kidney embryonic cell line 293-EBNA (Invitrogen) using the cationic lipid DOTAP (Boehringer Mannheim). The cell culture media were changed 24 hr after transfection into a serum-free medium AIM V (Life Technologies) before addition of compounds or TNF-α (PeproTech) at the appropriate concentrations. AP activity measured by a colorimetric assay (Berger et al., *Gene* 66:1–10, 1988) was performed 19–24 hr later.

Stable cell lines 293tar, 293tat and 293tat2 were generated by transfections using conditions described in (Tate et al., *FASEB J.* 4:227–231, 1990) with the plasmid pHIV.AP alone or along with either pHIV.tat or pSV2tat72, respectively. The assay of HIV-1 p24 antigen expression in the chronically HIV-1-infected promonocytic line U1 after 4 days and in acutely infected peripheral blood lymphocytes (PBL) after 7 days were described (Peterson et al., *J. Clin. Invest.* 89:574–580, 1992, and Brighty et al., *Proc Natl. Acad. Sci. USA* 88:7802–7805, 1991).

Formulation and Dosage

It will be recognized by one of skill in the art that the form and character of the pharmaceutically acceptable carrier or diluent is dictated by the amount of active ingredient with which it is to be combined, the route of administration and other well-known variables. A therapeutic compound or a pharmaceutically acceptable salt or hydrate or solvate thereof is administered in a virally infected patient (e.g., a HIV seropositive human) in an amount sufficient to prevent or delay the occurrence of further viral infection and clinical symptoms of the virally-mediated disease (e.g., AIDS). The route of administration of the compound is not critical but is usually oral or parenteral, preferably oral. The term parenteral, as used herein, includes intravenous, intramuscular, subcutaneous, intranasal, intrarectal, transdermal, opthalmic, intravaginal or intraperitoneal administration. The subcutaneous and intramuscular forms of parenteral administration are generally preferred. The daily parenteral dosage regimen will preferably be from about 0.01 mg/kg to about 25 mg/kg of total body weight, most preferably from about 0.1 mg/kg to about 4 mg/kg. Preferably, each parenteral dosage unit will contain the active ingredient in an amount of from about 0.1 mg to about 400 mg. The compounds are generally active when given orally and can be formulated as liquids, for example, syrups, suspensions or emulsions, tablets, capsules and lozenges. A liquid formulation will generally consist of a suspension or solution of the compound or pharmaceutically acceptable salt in a suitable liquid carrier(s), for example, ethanol, glycerine, non-aqueous solvent, for example polyethylene glycol, oils, or water with a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule. Alternatively, a dispersion or suspension can be prepared using any suitable pharmaceutical carrier(s), for example, aqueous gums, celluloses, silicates or oils and the dispersion or suspension then filled into a soft gelatin capsule. The daily oral dosage regimen will preferably be from about 0.01 mg/kg to about 40 mg/kg of total body weight. Preferably, each oral dosage unit will contain the active ingredient in an amount of from about 0.1 mg to about 1000 mg.

It will be recognized by one of skill in the art that the optimal quantity and spacing of individual dosages of a compound or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment (i.e., the number of doses of a compound or a pharmaceutically acceptable salt or hydrate or solvate thereof given per day and duration of therapy) can be ascertained by those skilled in the art using conventional course of treatment determination tests. In addition, the compounds of the invention can be co-administered with further active ingredients, such as zidovudine, gancyclovir and other compounds with known anti-viral activity mediated by a different mechanism of action than prevention of virion production in infected cells.

Without further elaboration, it is believed that one skilled in the art can, using the preceding description, utilize the invention to its fullest extent. The following examples are, therefore, to be construed as merely illustrative and not a limitation of the scope of the invention in any way.

EXAMPLE 1

This example illustrates AP reporter gene activity in 293-EBNA cells transiently transfected with pHIV.AP alone or in combination with pSVtat72. The expression level of AP increased by more than 50 fold in the presence of the tat expression vector, indicating transactivation of the HIV-LTR promoter by the 72 amino acid tat protein (FIG. 1).

Figure 2:
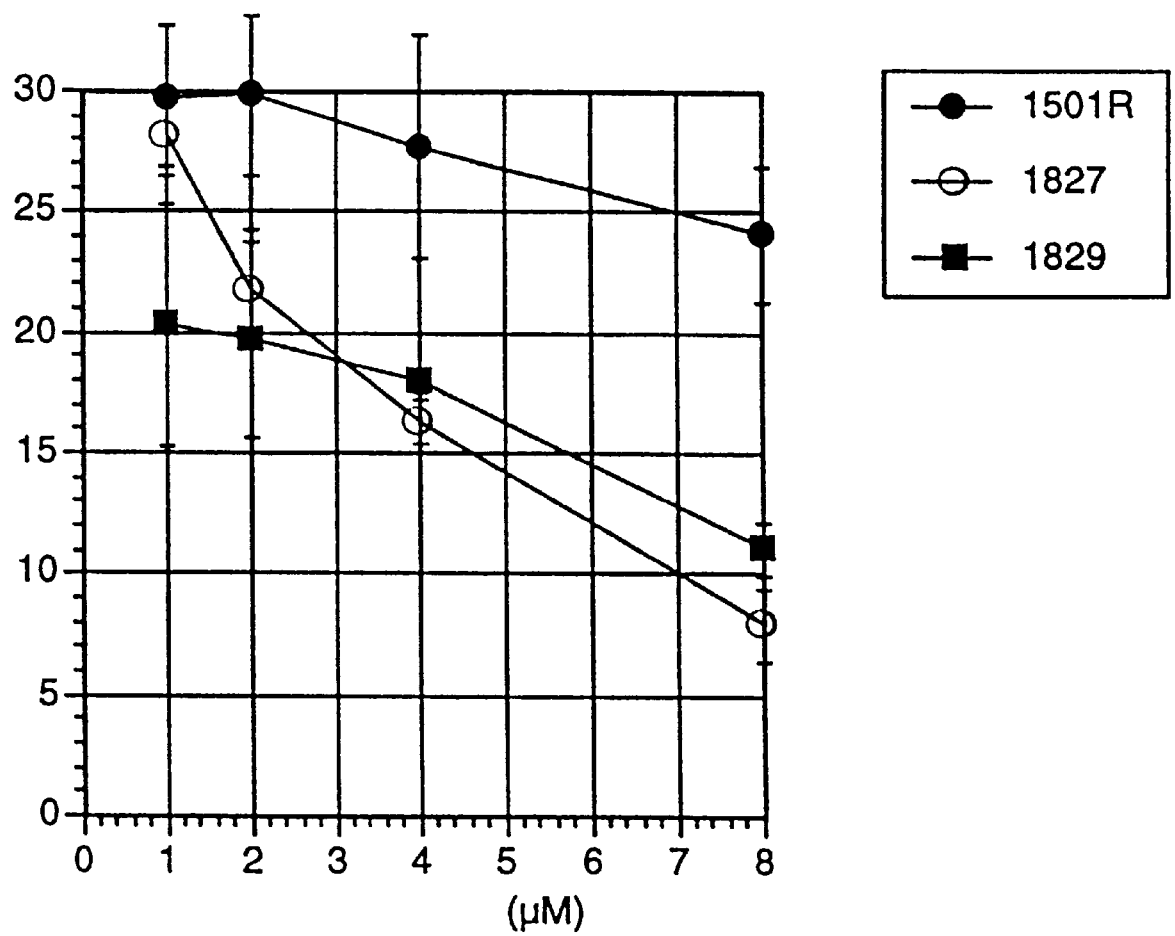
FIG. 2 shows an example of assay results of three compounds (CT1501R, CT1827, and CT1829, see Table 2 for chemical structures). Both CT1827 and CT1829 inhibited AP reporter gene expression in 239-EBNA cells with $ID_{50}$ values in the range of 4 to 6 $\mu$M using the HIV-LTR promoter construct transfected with a tat expression vector. No appreciable inhibition of AP expression was observed with CT1501R.

When three compounds (CT1501R, CT1827, and CT1829, see Table 1 for chemical structures) were added at various concentrations that are likely to be clinically achievable, both CT1827 and CT1829 inhibited AP reporter gene expression in 239-EBNA cells with $ID_{50}$ values in the range of 4 to 6 μM using the HIV-LTR promoter construct transfected with a tat expression vector. No appreciable inhibition of AP expression was observed with CT1501R (FIG. 2).

Figure 3:
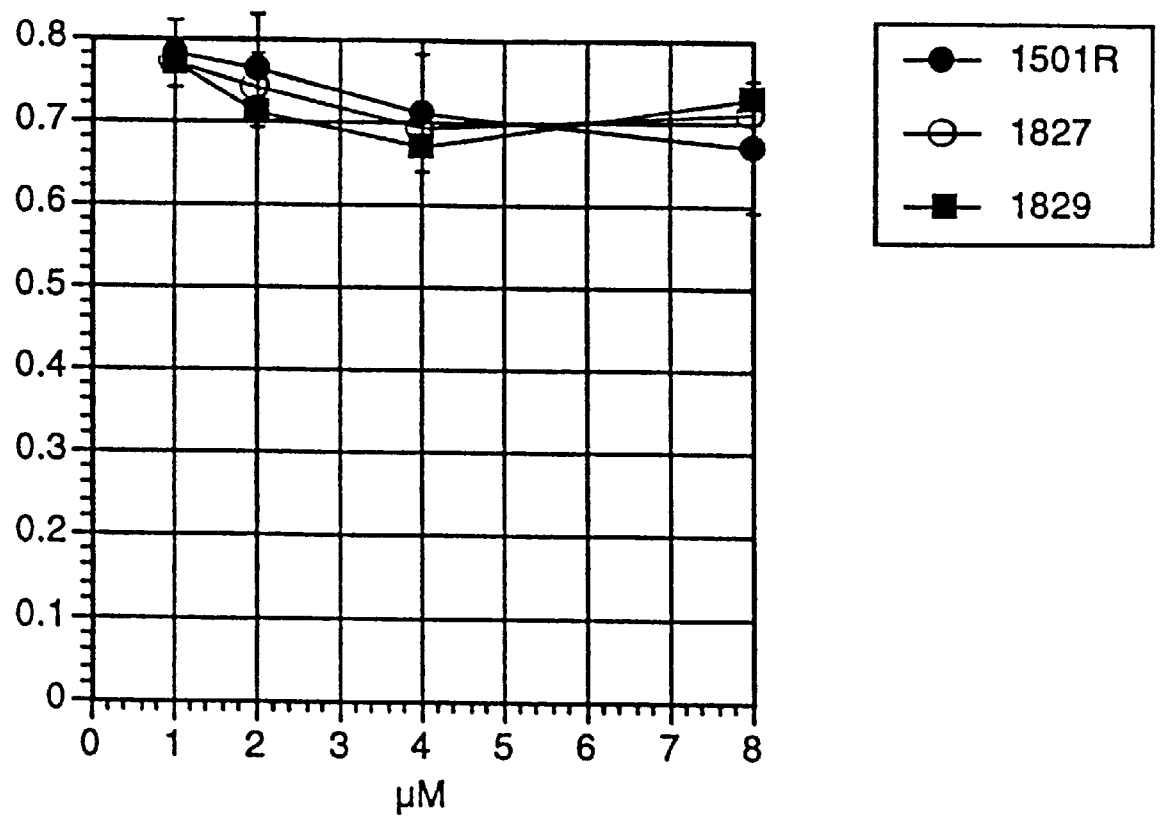
FIG. 3 shows the results of the above-noted compounds on viability of 293-EBNA cells. Cell viability was determined with a colorimetric assay using the tetrazolium salt of MTS (Promega) to report cell proliferation, viability and cytotoxicity. MTS indicates cell activity by serving as a substrate for mitochondria dehydrogenases for formation of soluble formazan dyes which can be quantitated by determining the absorbance at 490 nm using a plate reader. None of the three compounds tested in FIG. 2 showed significant cytotoxic effect on 293-EBNA cells as the concentrations indicated.

FIG. 3 shows the results of the three compounds on viability of 293-EBNA cells. Cell viability was determined with a calorimetric assay using the tetrazolium salt of MTS (Promega) to report cell proliferation, viability and cytotoxicity. MTS indicates cell activity by serving as a substrate for mitochondria dehydrogenases for formation of soluble formazan dyes which can be quantitated by determining the absorbance at 490 nm using a plate reader. None of the three compounds tested showed significant cytotoxic effect on 293-EBNA cells as the concentrations indicated in FIG. 3.

EXAMPLE 2

Figure 4:
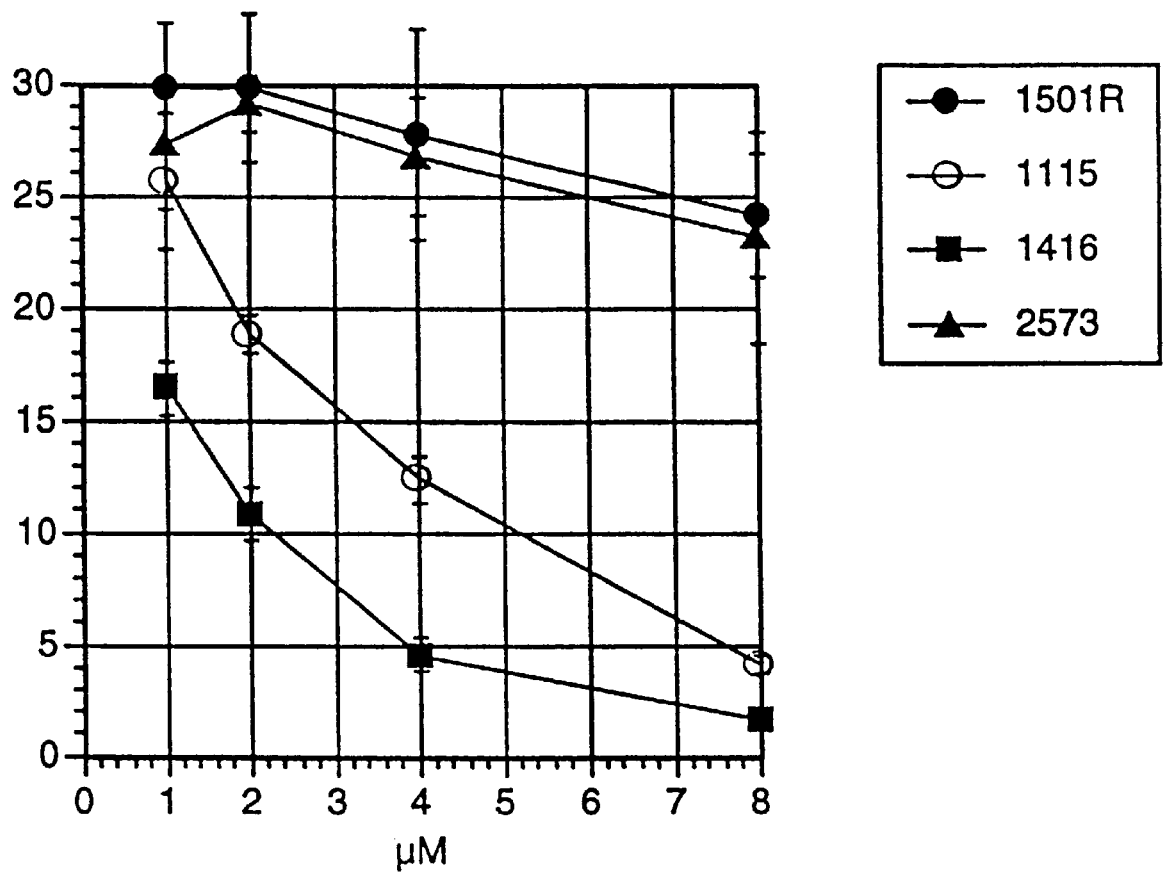
FIGS. 4 and 5 show another example of assay results of three other compounds (see Table 1 for chemical names). CT1501R (again) and CT2573 did not affect AP activity and cell viability significantly, whereas CT1416 and CT2573 (structurally related to CT1827 and CT1829) were able to inhibit AP expression by 50% at concentrations in the range of 1 to 4 µM. However, some cytotoxicity was noted with CT1416 and CT2573 with cellular $LD_{50}$ values at around 5 µM.
Figure 5:
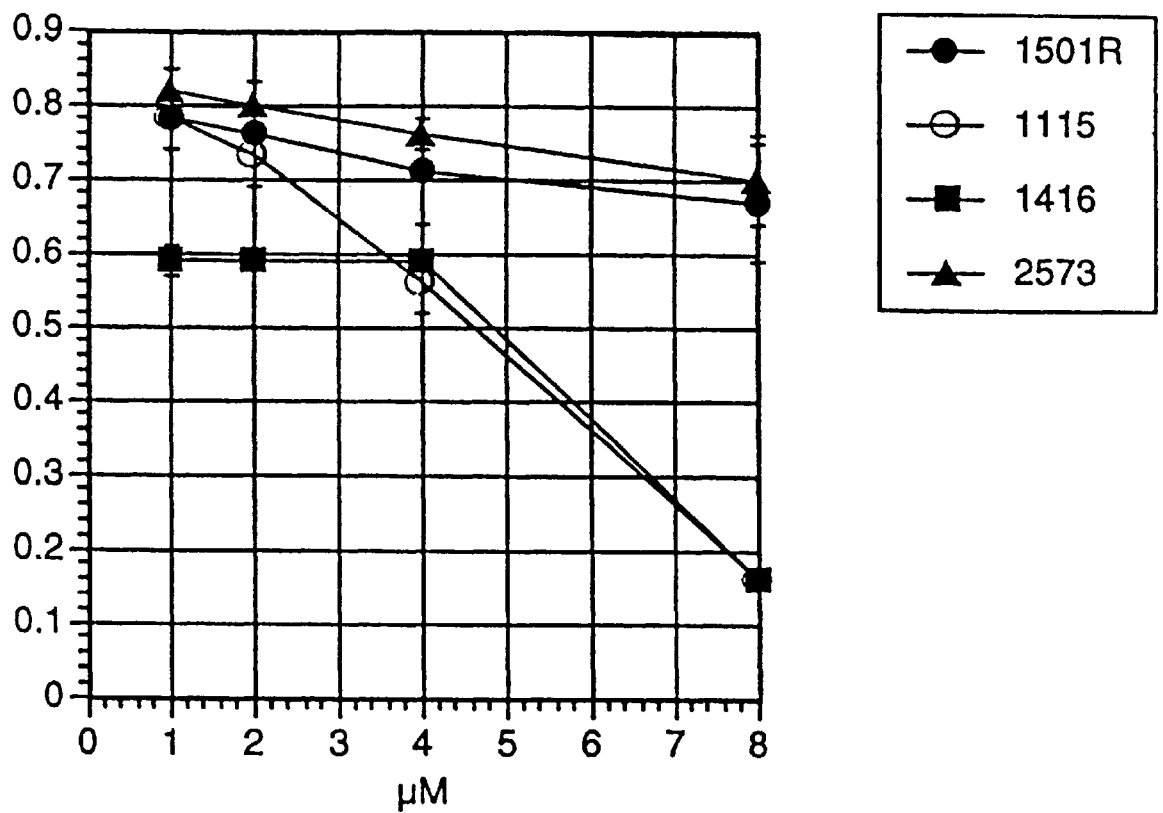

This example illustrates assay results of four compounds (CT1501R, CT1115, CT1416 and CT2573, see Table 1 for chemical names) for AP reporter gene activity in 293-EBNA cells transiently transfected with pHIV.AP alone or in combination with pSVtat72. CT1501R (again) and CT2573 did not affect AP activity and cell viability significantly, whereas CT1416 and CT2573 were able to inhibit AP expression by 50% at concentrations in the range of 1 to 4 μM (FIG. 4). However, some cytotoxicity was noted with CT1416 and CT2573 with cellular $LD_{50}$) values at around 5 μM (FIG. 5).

EXAMPLE 3

Figure 6:
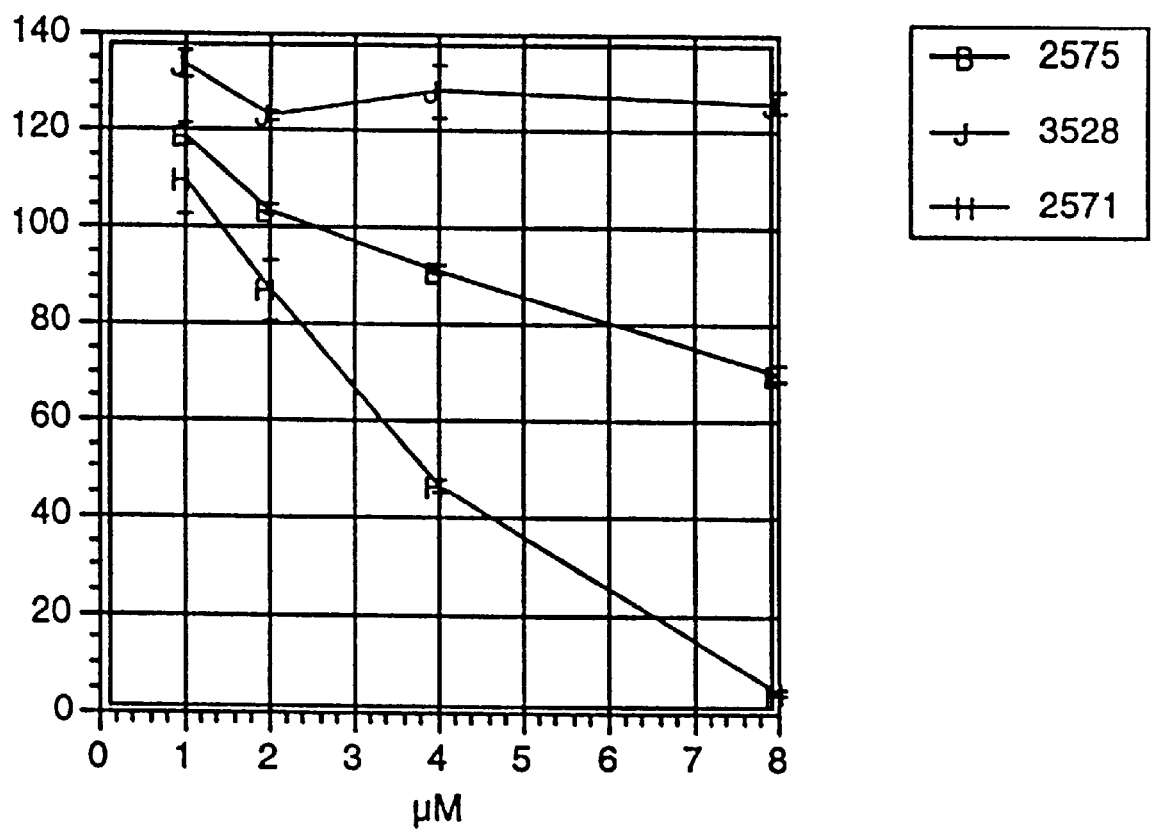
FIG. 6 shows an example of the effect three amino-alcohol-substituted xanthine compounds (CT2575, CT3528, and CT2571) on AP reporter gene activity in 293-EBNA cells stably transfected with pCMV.AP. CT2575 and CT2571 inhibited AP reporter gene expression in 293-EBNA cells with $IC_{50}$ values of 3 µM and 8 µM, respectively. No appreciable inhibition of AP expression was detected when using the compound CT3528.

This example illustrates assay results of three amino-alcohol-substituted xanthine compounds (CT2575, CT3528, and CT2571) on AP reporter gene activity in 293-EBNA cells stably transfected with PCMV.AP. CT2575 and CT2571 inhibited AP reporter gene expression in 293-EBNA cells with $IC_{50}$ values of 3 μM and 8 μM, respectively. No appreciable inhibition of AP expression was detected when using the compound CT3528 (FIG. 6).

Figure 7:
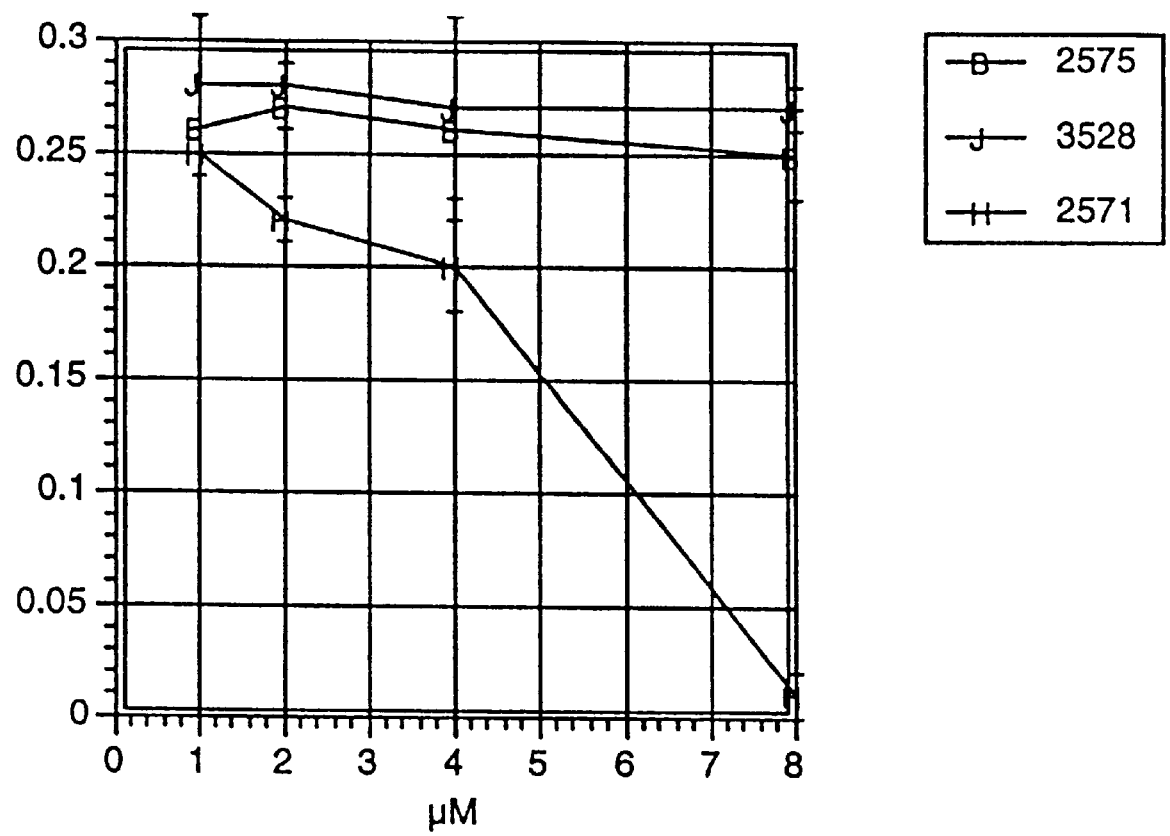
FIG. 7 shows the effect of the three compounds shown in FIG. 6 on the viability of 293-EBNA cells. Cell viability was measured by a colorimetric assay that uses Alamar Blue dye (Alamar, Inc.) to report cell proliferation, viability and cytotoxicity. This vital dye indicates cell activity by serving as substrate for mitochrondrial dehydrogenases for the formation of soluble dyes which can be quantitated by determining the difference in absorbance between A570 and A600 using a plate reader. CT2571 was found to be cytotoxic to 293-EBNA cells while CT2575 and CT3528 showed no significant cytotoxic effect on 293-EBNA cells at the concentrations indicated.

Cell viability was measured by a calorimetric assay that uses Alamar Blue dye (Alamar, Inc.) to report cell proliferation, viability and cytotoxicity. This vital dye indicates cell activity by serving as substrate for mitochrondrial dehydrogenases for the formation of soluble dyes which can be quantitated by determining the difference in absorbance between A570 and A600 using a plate reader. CT2571 was found to be cytotoxic to 293-EBNA cells while CT2575 and CT3528 showed no significant cytotoxic effect on 293-EBNA cells at the concentrations indicated (FIG. 7).

EXAMPLE 4

Figure 8:
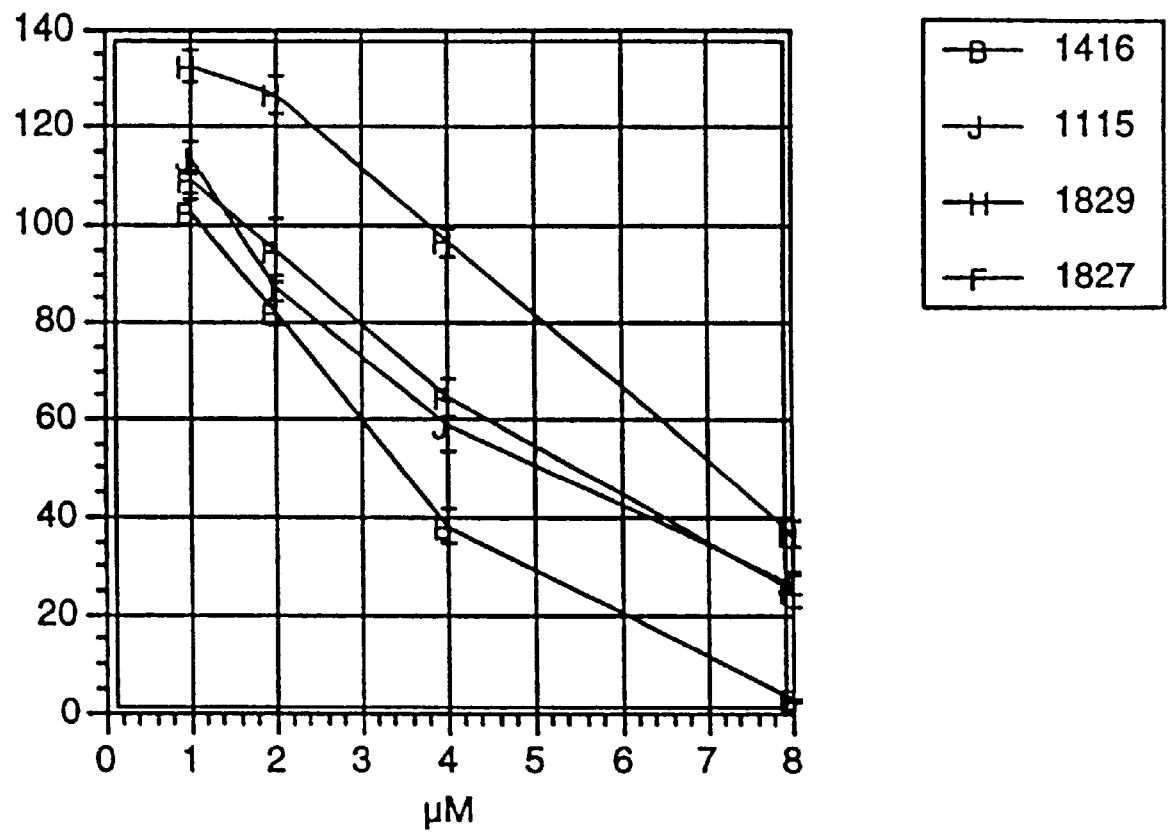
FIGS. 8 and 9 show another example of the CMV assay results (as shown in FIGS. 6 and 7) of four other amino alcohol-substituted compounds. While all four compounds were able to inhibit AP activity by 50% in the range of 2 to 6 µM, CT1416 and CT1115 were found to be cytotoxic with an $LD_{50}$ value of about 5 µM, whereas CT1827 and CT1829 showed no significant cytotoxic effect on 293-EBNA cells at the concentrations indicated. Therefore, a significant therapeutic window exists.
Figure 9:
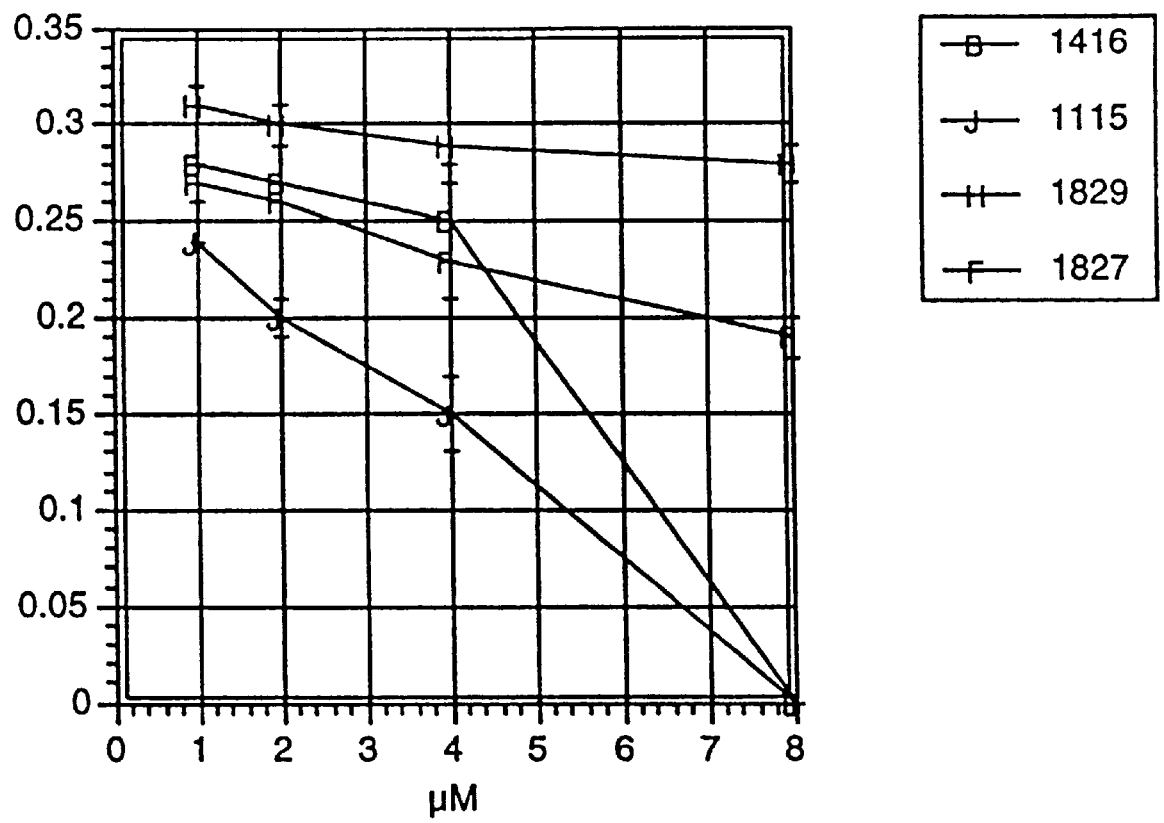

This example illustrates assay results of the CMV assay results for four different amino alcohol-substituted heterocyclic compounds (CT1416, CT1115, CT1829 and CT1827). While all four compounds were able to inhibit AP activity by 50% in the range of 2 to 6 μM (FIG. 8), CT1416 and CT1115 were found to be cytotoxic with an $LD_{50}$ value of about 5 μM (FIG. 9). CT1827 and CT1829 showed no significant cytotoxic effect on 293-EBNA cells at the concentrations indicated. Therefore, a significant therapeutic window exists.

EXAMPLE 5

Figure 10:
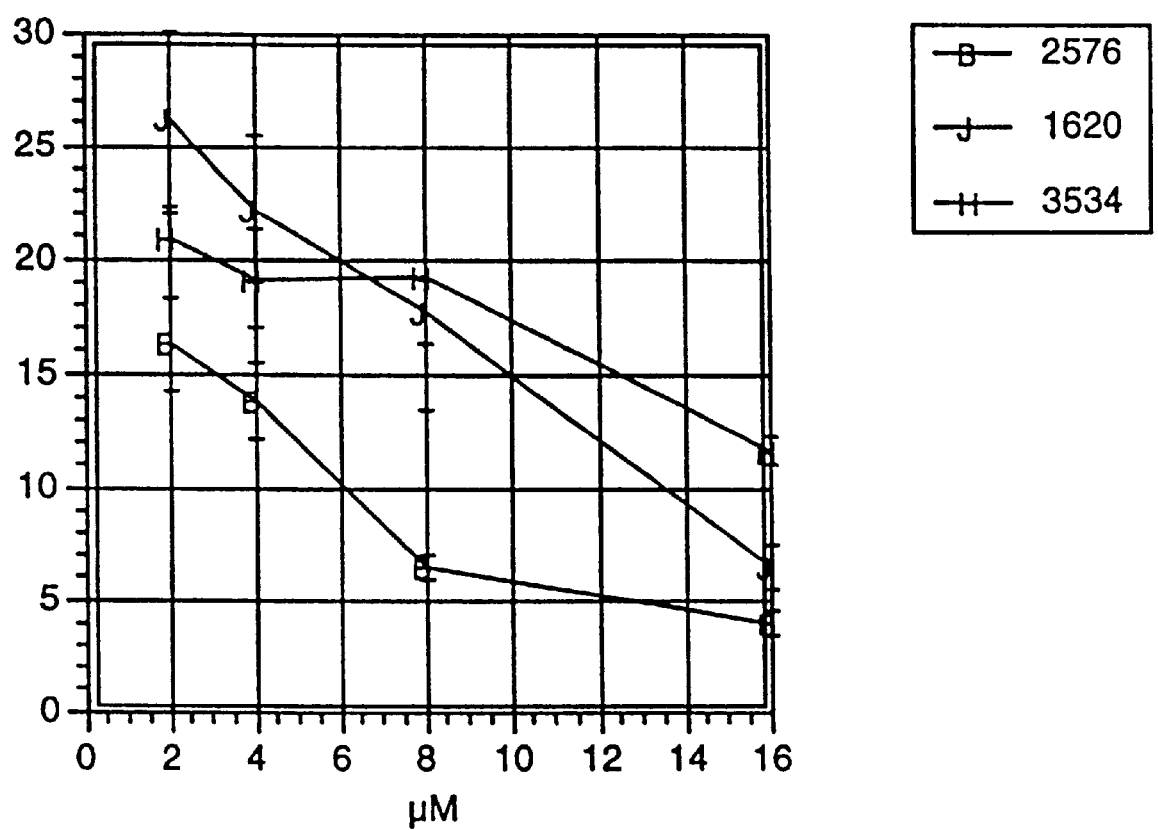
FIG. 10 shows an example of assay results of three compounds (CT2576, CT1620, and CT3534, see Table 1 for chemical structures). CT2576 inhibited AP reporter gene expression in 239-EBNA cells with ID50 values in the range of 4 to 6 µM using the HIV-LTR promoter construct transfected with a tat expression vector.

This example illustrates assay results of three compounds (CT2576, CT1620, and CT3534, see Table 1 for chemical structures) in a tat activation of HIV-LTR promoter in EB293 cells. CT2576 inhibited AP reporter gene expression in 239-EBNA cells with $ID_{50}$ values in the range of 4 to 6 μM using the HIV-LTR promoter construct transfected with a tat expression vector (FIG. 10).

Figure 11:
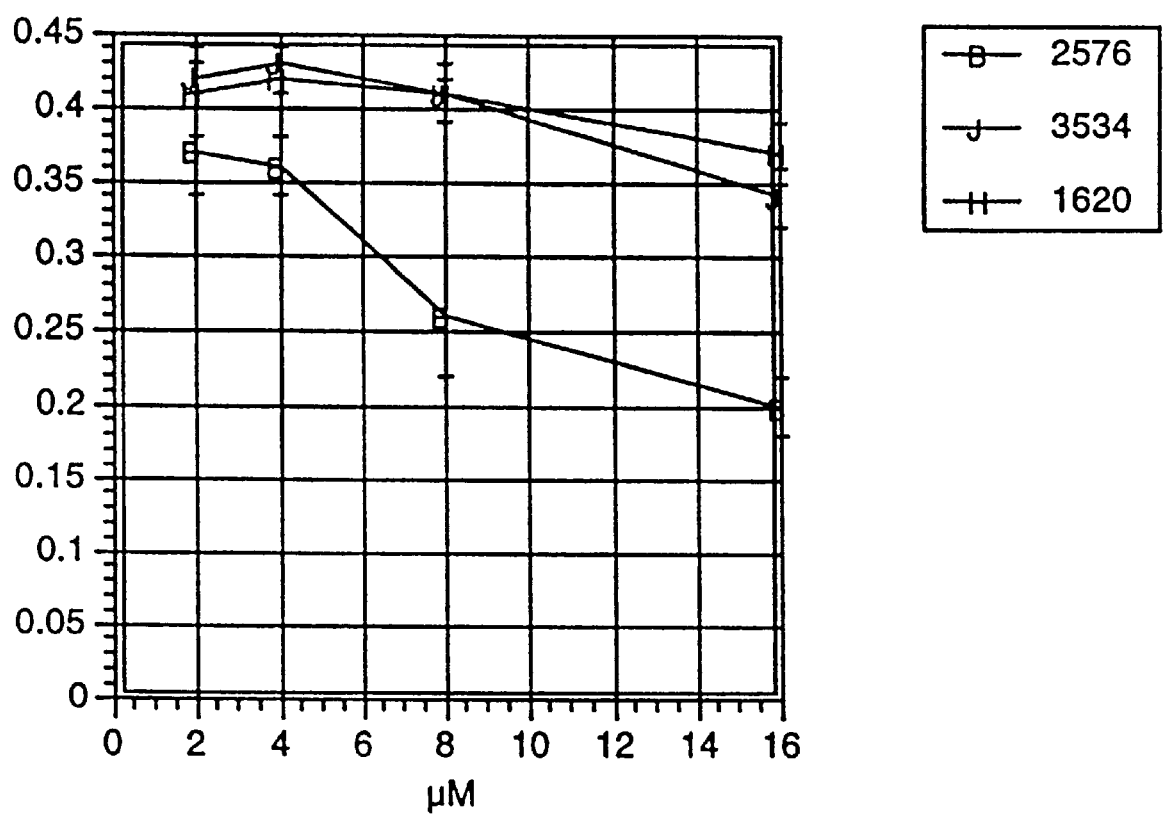
FIG. 11 shows the results of the above-noted compounds in FIG. 10 on viability of 293-EBNA cells. Cell viability was determined with a colorimetric assay using the tetrazolium salt of MTS (Promega) to report cell proliferation, viability and cytotoxicity. MTS indicates cell activity by serving as a substrate for mitochondria dehydrogenases for formation of soluble formazan dyes which can be quantitated by determining the absorbance at 490 nm using a plate reader. None of the three compounds tested in FIG. 10 showed significant cytotoxic effect on 293-EBNA cells at the concentrations indicated.

Cell viability was determined with a colorimetric assay using the tetrazolium salt of MTS (Promega) to report cell proliferation, viability and cytotoxicity. MTS indicates cell activity by serving as a substrate for mitochondria dehydrogenases for formation of soluble formazan dyes which can be quantitated by determining the absorbance at 490 nm using a plate reader. None of the three compounds tested showed significant cytotoxic effect on 293-EBNA cells at the concentrations indicated (FIG. 11).

EXAMPLE 6

This example illustrates assay results of an assay with HIV-infected U1 cells where measurement of HIV-1 expression in response to an exogenous stimulant was determined. Viral release was measured by determining the amount of HIV-1p24 antigen (Ag) expression in cell culture supernatants. Compounds CT1501R, CT1829, CT1411 and CT2576 all suppressed HIV-1 expression, but CT2576 was the most effective and CT1827 showed some cytotoxicity (FIG. 12, top panel).

Figure 12A:
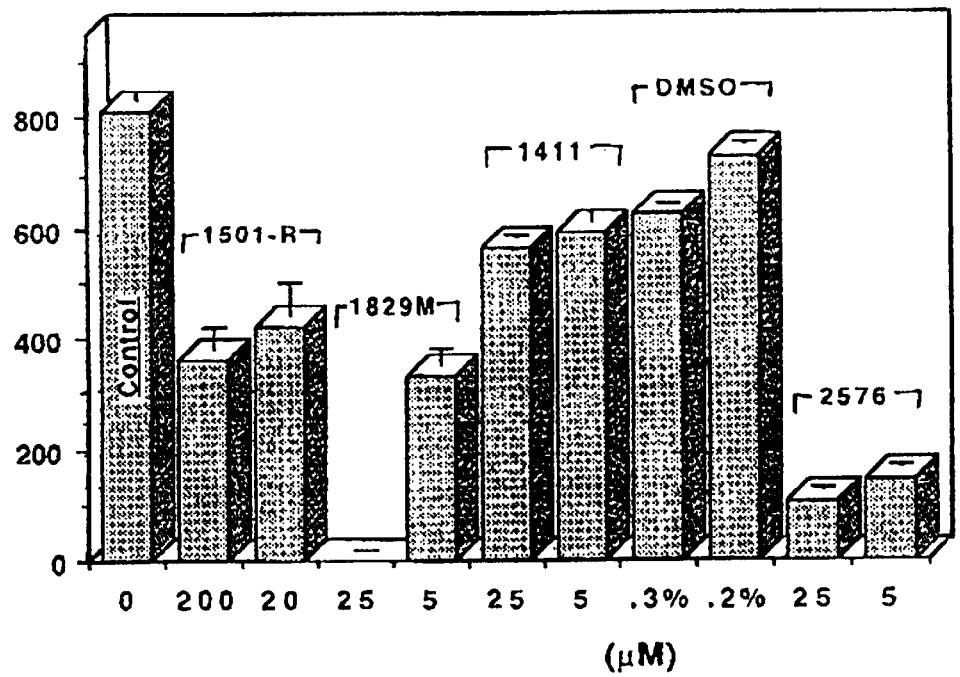
FIG. 12 (top panel) shows the results of an assay with HIV-infected U1 cells where measurement of HIV-1 expression in the presence of various compounds was determined. Viral release was measured by determining the amount of HIV-1 p24 antigen (Ag) expression in cell culture supernatants. Compounds CT1501R, CT1829, CT1411 and CT2576 all suppressed constitutive HIV-1 expression when plated at high density initially, but CT2576 was the most effective and CT1827 showed some cytotoxicity.
Figure 12B:
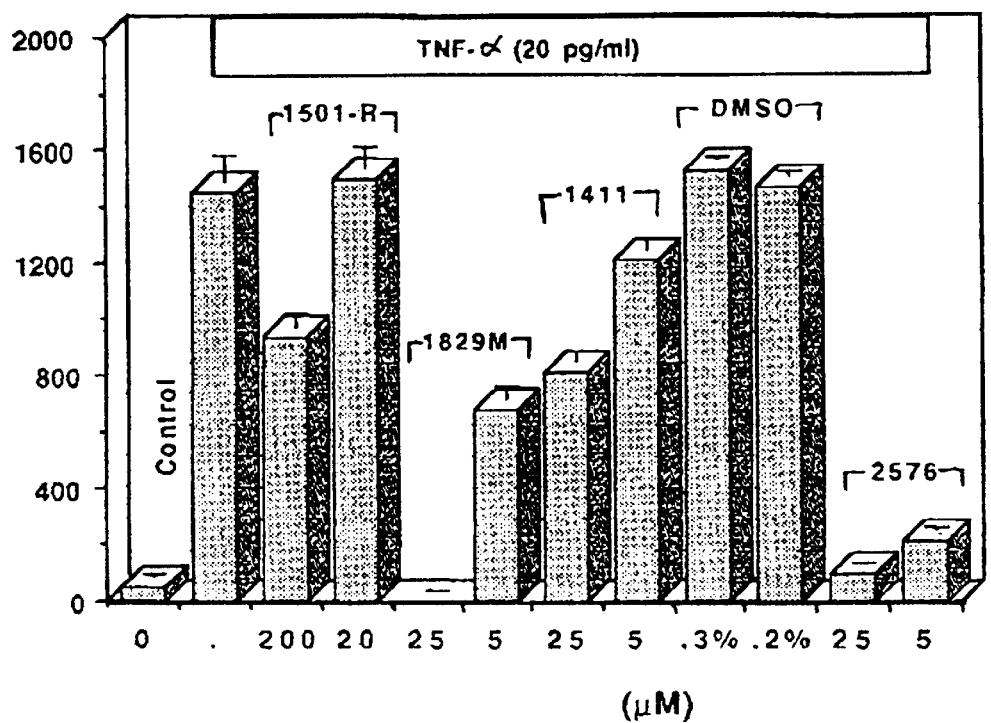

FIG. 12 bottom panel shows the effect of several compounds on TNFα mediated upregulation of HIV-1 in U1 cells. TNFα is a potent stimulus of viral expression. Again, CT1501R, CT1829, CT1411 and CT2576 all suppressed HIV-1 expression, but CT2576 was the most effective and CT1827 showed some cytotoxicity at a 25 μM concentration.

EXAMPLE 7

This example illustrates that CT2576 suppressed both tat-dependent and TNF-α induced HIV-LTR transcription with an $IC_{50}$ of approximately 10 μM. Study of the effects of CT2576 on cell toxicity was performed using the Alamar Blue™ dye (Alamar Biosciences) according to the manufacturer's instructions. CT2576 was not toxic to 293-EBNA cells at concentrations up to 35 μM. To show CT2576 can inhibit HIV expression, CT2576 was tested for the ability to block HIV p24 antigen expression in chronically or acutely infected cells. Specifically, CT2576 inhibited the TNF-α and IL-6 induced and the constitutive expression of HIV in the chronically infected U1 cells and in peripheral blood lymphocytes (PBL) freshly infected with a HIV strain from a clinical isolate with an $IC_{50}$ of approximately 1 μM. Pharmacological inhibition of synthesis of selected PL may therefore be a novel therapeutic approach to suppression of HIV replication.

CT2576 altered the pattern of PA composition in 293tat cells. One of the steps after cell activation involves the hydrolysis of phosphatidylcholine (PC), the major phospholipid of cellular membranes, by phospholipases C and D, leading to the generation of second messengers, such as PA and DG, in the signal transduction cascade. HPLC analysis of the total cellular phospholipid content (by the method described herein) of 293tat cells showed several difference in specific subspecies of PA After brief TNF-α stimulation (45 sec), a $C_{14-16}$ highly saturated acyl chain peak of PA (Rf 6–7 min.) increased up to 80%. This peak changed from 5.4% to 9% of the total far UV absorbing lipids at this time. In contrast, a PA peak comprised mainly of $C_{18}$ and $C_{20}$ unsaturated acyl chains (Rf 9.5–10.5 min.) was absent in 293tat cells. Preincubation of these cells with 8 μM CT2576 altered the PA composition of these cells. The short chained saturated PA subspecies was less after CT2576 preincubation than without treatment and showed very little change with addition of TNF-α. The long chain unsaturated PA comprised 15% of the far UV absorbing lipids after preincubation with CT2576 and it increased to 20% after 2 minutes of stimulation with TNF-α. CT2576 affected the turnover of PA subspecies in 293tat cells.

EXAMPLE 8

This example illustrates that CT2576 inhibited TNF-α and tat-activated HIV-LTR promoter directed expression in 293tat cells. Cell activation signals generated by interaction of ligands with receptors are eventually converted to changes in the pattern of gene expression. A reporter gene expression system under the control of the HIV-LTR promoter was set up to investigate compounds that inhibit signaling pathway for HIV activation in infected cells. Stably transfected cell lines containing the plasmid constructs, pHIV.AP, using the HIV-LTR promoter to direct the expression of AP reporter gene and pSV2tat72 or pHIV.tat, expression vectors for the first exon of tat protein from HIV were used to study the effects of various concentrations of CT-2576 on AP expression.

Figure 14:
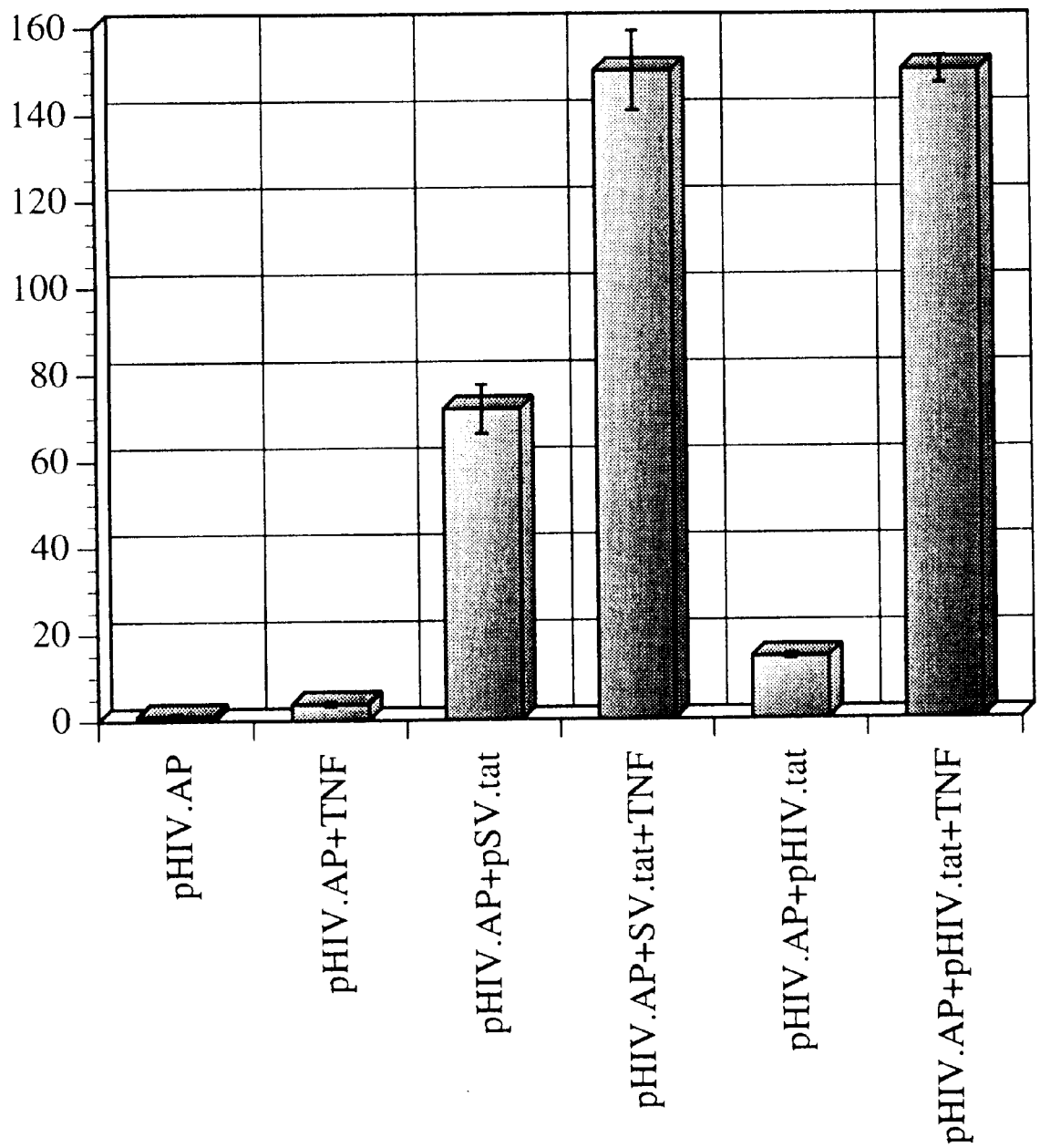
FIG. 14 illustrates the effect of tat and TNF-α on HIV-LTR-mediated reporter gene expression in 293-EBNA cells. The y-axis refers to the relative amount of AP reporter gene activity present in the culture media of 293-EBNA cells after transient transfection with various plasmids. Freshly trypsinized 293-EBNA cells at $10^4$ cells per sample were transfected with 2 µg of either pHIV.AP, pHIV2.AP, or pHIV3.AP alone or in combination with pSV2tat72 or pHIV.tat using the cationic lipid DOTAP. The plasmids pHIV.AP, pHIV2.AP, and pHIV3.AP contain nucleotides −453 to +80, −107 to +80, and −80 to +80 of the HIV-LTR sequence respectively. Transfected cells were plated in 96-well microtiter plates at 2,000 cells per well. The cell culture media were changed 24 hr later into new medium. The samples were incubated for another 24 hr with or without TNF-α (20 ng/ml). 2 µl of medium from each well was used for AP assay. The height of each column represents the mean of triplicate samples with error bar indicating the standard deviation of the mean.

AP reporter gene activity expressed in 293-EBNA cells transfected with either pHIV.AP alone or in combination with pSV2tat72, pHIV.tat or with TNF-α stimulation is shown in FIG. 14. The plasmid pHIV.AP contains the full-length HIV-LTR sequence that extends from nucleotides −453 to +80. The expression level of AP was low using the pHIV.AP construct alone, indicating the presence of negative regulatory elements in the HIV-LTR sequence. Induction with TNF-α increased the AP expression level by about 4 fold. The AP expression level increased by 15 to 70 fold in the presence of the tat expression plasmids pHIV.tat or pSV2tat72. The tat-expression plasmid regulated by the SV40 early promoter has been reported to be more potent than the one directed by HIV-LTR in cotransfection assays in MDA468 cells (Nabell et al., *Cell Growth & Differentiation* 5:87–93, 1994). TNF-α and tat in combination enhanced the AP expression level by two fold when using the pSV2tat72 construct, and by ten fold when using the pHIV.tat construct, but the final levels of AP activity were similar.

Figure 15:
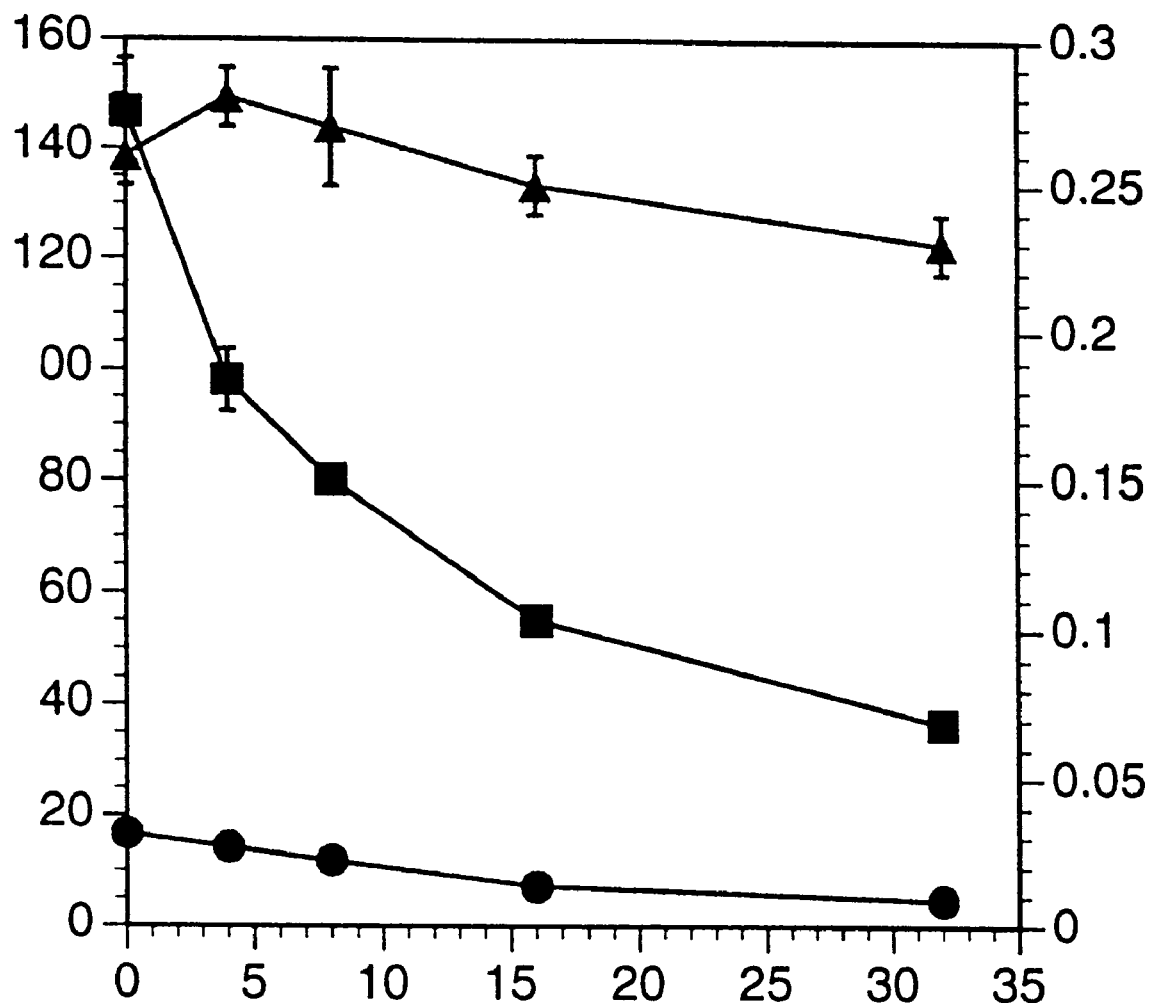
FIG. 15 shows the effect of CT2576 on HIV-LTR expression activated by tat and TNF-α in 293tat cells. 293tat cells, a cell line stably transfected with the expression plasmids pHIV.AP and pHIV.tat, were plated onto 96-well microtiter plates at 2000 cells per well. The media were changed the next day and CT2576 was added at the indicated concentrations to the fresh media with or without TNF-α (20 ng/ml). 2 µl of medium from each well was used for AP assay 24 hr later. After culture media were withdrawn for AP assay, cytotoxicity was measured for the same cell cultures using an indicator dye, Alamar Blue™, that would change color in response to the reduction potential of cell medium due to cell growth. The left y-axis refers to the absorbance value of the reduced form of Alamar Blue™ at 570 nm with the background absorbance at 600 nm from the oxidized form of Alamar Blue™ subtracted. Each data point represents the mean of triplicate samples with error bar indicating the standard deviation of the mean.

The effect of CT2576 on HIV promoter activity in 293tat cells, with the HIV.AP construct cotransfected with pHIV.tat, is shown in FIG. 15. CT2576 inhibited AP reporter gene expression by 50% with an inhibition constant ($IC_{50}$) in the range of 10 μM with or without TNF-α induction. The inhibition of AP expression is the result of two events: a decrease in AP expression and a decrease in tat expression and therefore lower tat protein levels for transactivation. The measurement of 293tat cells viability using Alamar Blue™ indicated CT2576 was not cytotoxic at concentrations up to 32 μM.

EXAMPLE 9

This example illustrates that CT2576 did not affect the activation of NFκB in 293tat cells. As NFκB is the major transcription factor involved in the activation of HIV-LTR promoter by TNF-α (Baeuerle et al., *Annu. Rev. Immunol.* 12:141–179, 1994), the inhibition of TNF-α signaling by CT2576 shows that CT2576 interacted with a step in the signal transduction pathway leading to the activation of NFκB. Electrophoretic mobility shift assay (FIG. 16) showed NFκB was activated in 293tat cells upon induction with either TNF-α or IL-1β, and CT2576 did not inhibit TNF-α dependent activation of NFκB. Northern blot analysis (FIG. 16) again showed induction of AP transcripts with either TNF-α or IL-1β. However, not only was there no decrease in AP mRNA steady-state levels in the presence of CT2576, there was an increase in mRNA level despite an 83–90% decrease in AP activity after TNF-α or IL-1β induction in the presence of CT2576. Therefore, CT2576 blocked expression of AP as a post-transcriptional step.

EXAMPLE 10

Figure 17:
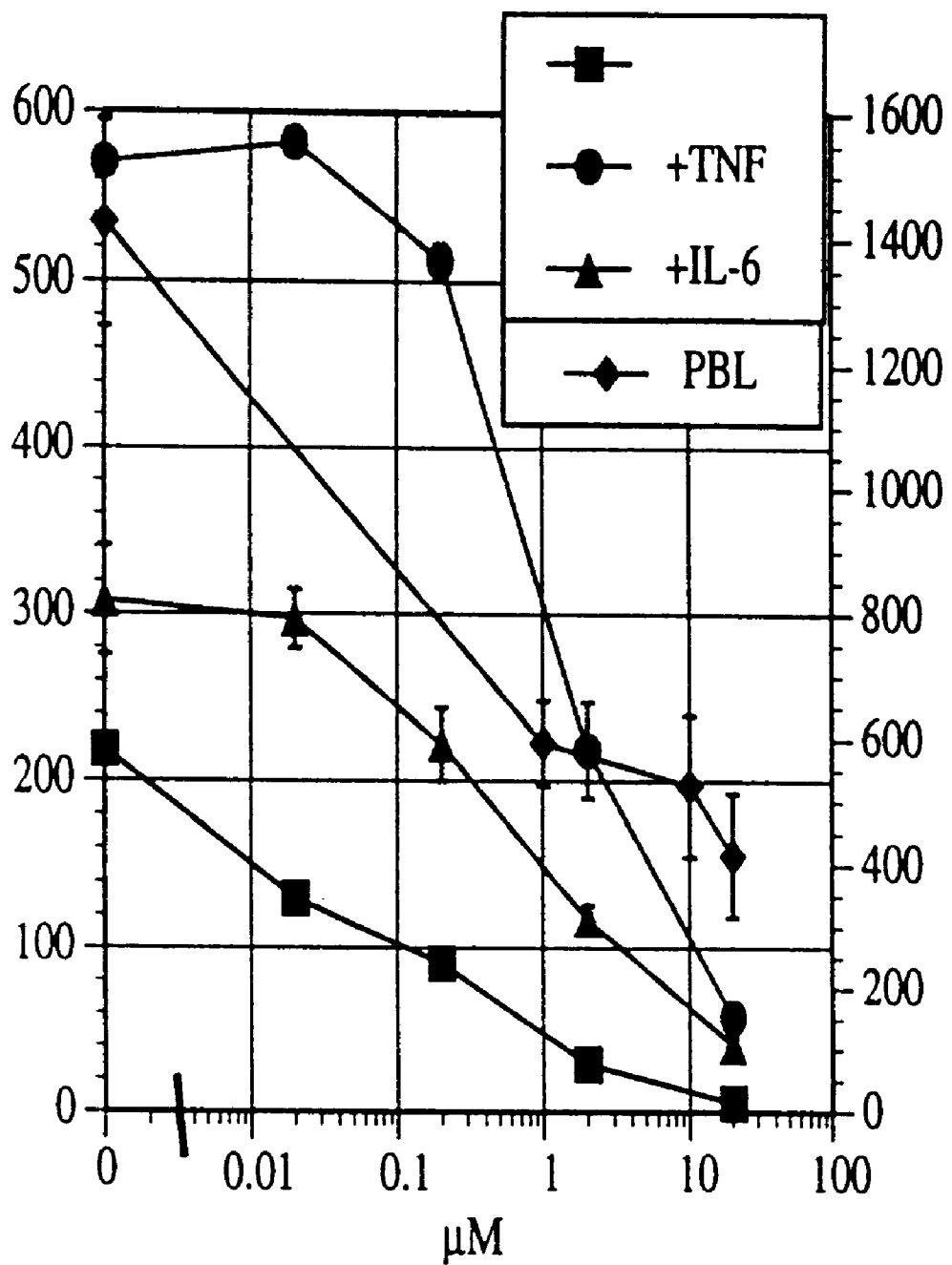
FIG. 17 illustrates a dose response curves of CT2576 on constitutive, TNF-α, and IL-6-mediated expression of HIV-1 in a chronically infected U1 cell line (left Y-axis) and of CT3537 on HIV expression in PBL acutely infected with the JR-CSF primary isolate (right Y-axis). U1 cells were incubated for four days after the addition of CT2576 with or without TNF-α (20 pg/ml) or IL-6 (1 ng/ml). PBL were inoculated with HIV at 10 ng virus/$10^6$ cells/well and incubated with various concentrations of CT3537 for 7 days. Each data point represents the average expression levels of HIV-1 p24-antigen in the cell supernatants measured by ELISA from triplicate samples with error bar indicating the SD.

This example illustrates that CT2576 inhibited both constitutive and cytokine-induced HIV expression in a chronically-infected U1 cell line. A chronically HIV-1 infected human promonocyte cell line, U1 (Poli et al., *J. Exp. Med.* 172:151–158, 1990), was used as a model to see if the inhibitory effect of CT2576 on HIV-LTR driven reporter gene expression could be extended to block HIV replication per se in infected cells. TNF-α and IL-6 have been reported to upregulate the expression of HIV-1 in U1 cells (Poli et al., *Proc Natl. Acad. Sci. USA* 91:108–112, 1994). U1 cells were plated onto 24-well microtiter plates to study the dose-response effect of CT2576 on the constitutive ($10^4$ cells/well), TNF-α or IL-6 mediated ($2 \times 10^3$ cells/well) expression of HIV-1. CT2576 was capable of inhibiting the constitutive, the TNF-α mediated, as well as the IL-6 mediated expression of HIV in U1 cells with an $IC_{50}$ value of less than 1 μM (FIG. 17).

CT3537 also inhibited HIV expression in acutely infected cells. For acute infection, the effect of an acetylated form of CT2576, CT-3537, was tested on PBL from a human donor freshly infected with a clinical isolate HIV-1 strain JR-CSF. Analysis of p24 antigen release 7 days after infection at various concentrations of CT3537 showed that CT3537 inhibited HIV expression with an $IC_{50}$ of less than 1 μM (FIG. 17).

EXAMPLE 11

Figure 13A:
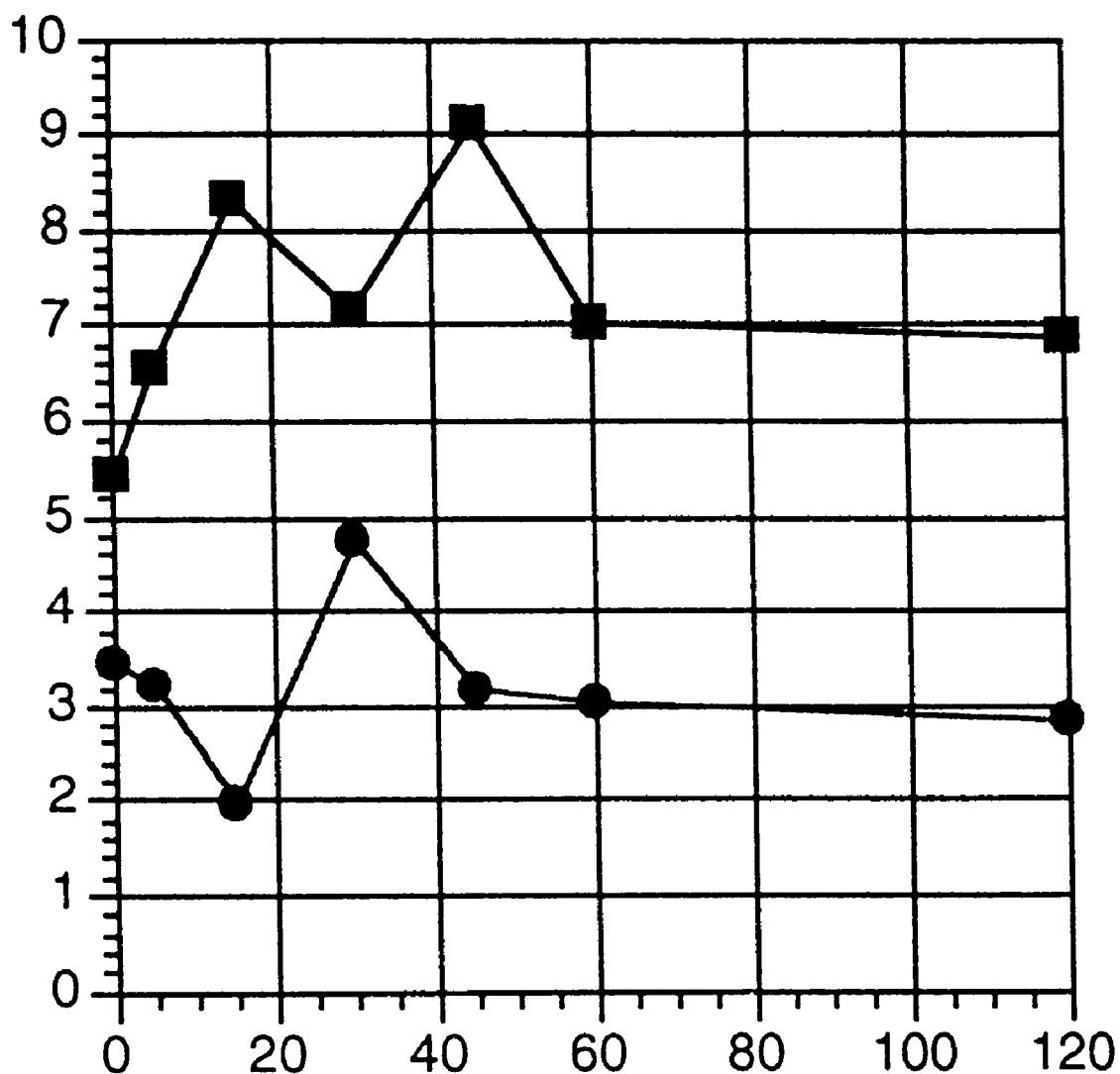
FIGS. 13A and 13B illustrate the effect of CT2576 on PA and DG generation.
Figure 13B:
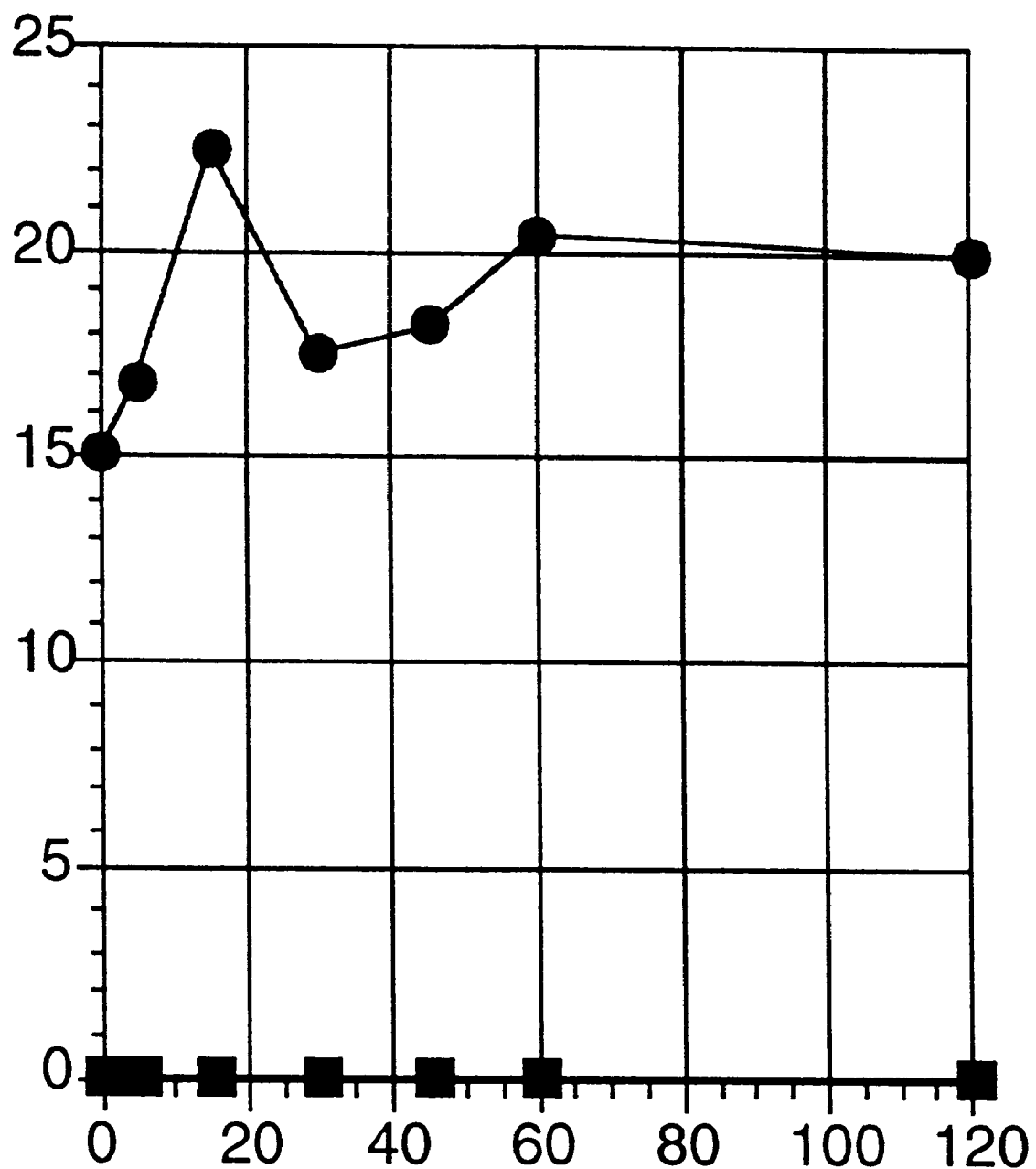
Figure 16:
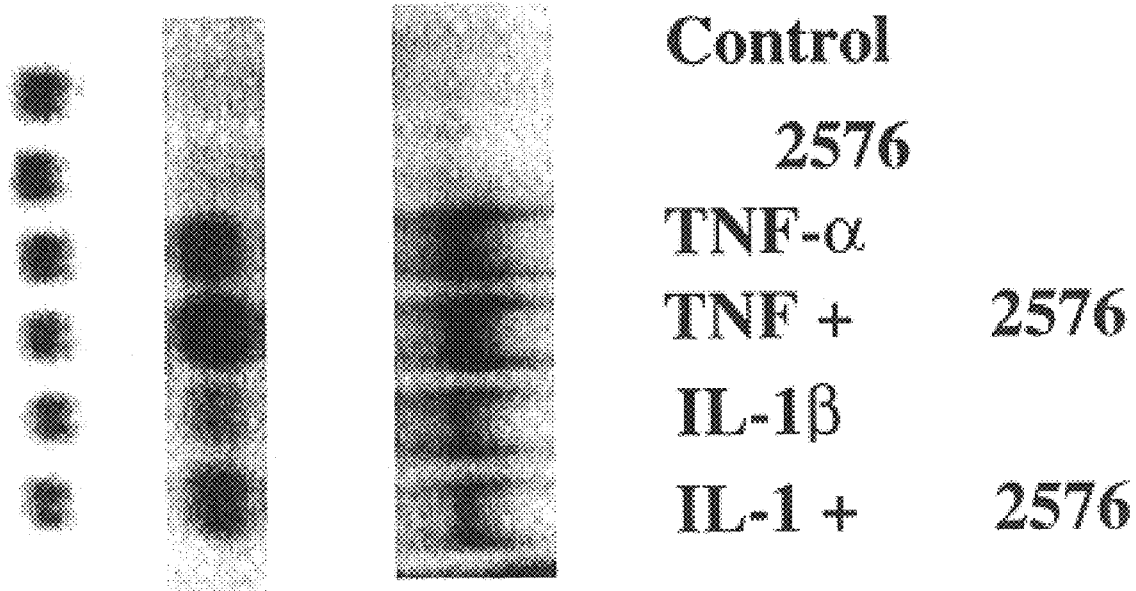
FIG. 16 shows the effect of CT2576 on NFκB activation and transcription. Nuclear extracts (A) from 293tat cells were tested by EMSA for activation of NFκB. A radiolabeled 40-mer covering the NFκB sequences in the HIV promoter was used as a probe. Cells were incubated with CT2576 at 12 µM, human TNF-α at 40 ng/ml or IL-1β at 1 ng/ml, or pre-incubated for 30 min. with CT2576 and then stimulated with TNF-α or IL-1β for 18 hr prior to making extracts. RNA was extracted from 293tat cells (B) after treatment with CT2576 without or with TNF-α or IL-1β for 18 hr. Northern blots analysis were performed using probes derived from AP cDNA and G3PDH cDNA as a control for normalization of mRNA level. AP activity was determined in cell supernatants from the various samples.

This example summarizes the data for the preferred embodiment, CT2576. CT2576, which affects the generation of myrPA species in 293tat cells (FIG. 13), inhibited tat and TNF-α induced activation of HIV-LTR directed AP expression with an $IC_{50}$ of 10 μM (FIG. 15) with minimal cytotoxic effect. Gel-shift assays and Northern blot analysis showed CT2576 did not block expression at the transcription stage (FIG. 16). Various mechanisms of post-transcriptional regulation of gene expression have been described (Rhoads, *J. Biol. Chem.* 268:3017–3020, 1993; Hawa et al., *J. Mol. Endocrinology* 10:43–49, 1993; Morandi et al., *J. Cell. Physiol.* 160:367–377, 1994; and Ito et al., *Proc Natl. Acad. Sci. USA* 91:7455–7459, 1994). The mechanism of action of CT2576 is therefore different from that of Ro 24–7429 (Hsu et al., *Proc Natl. Acad. Sci. USA* 90:6395–6399, 1993), a compound that blocks HIV-LTR promoter transcription through interaction with the tat protein, though both compounds were selected initially on their potential to inhibit tat activation of the HIV-LTR promoter using a reporter gene expression assay. As CT2576 blocks activation of the HIV-LTR expression post-transcriptionally, CT2576 has a synergistic effect with other anti-HIV compounds that act by different mechanisms. CT2576 is also effective in suppressing HIV expression in cell types with constitutive NFκB activity, such as certain neurons involved in the etiology of AIDS dementia complex (Kaltschmidt et al., *Mol. Cell. Biol.* 14: 3981–3992, 1994).

We studied the effect of CT-2576 on HIV expression in a chronically HIV-1 infected promonocytic U1 cell line (Folks et al., *Science* 238:800–802, 1987). Chronically infected monocytes or macrophages have been found to be a major source for HIV dissemination in the pathogenesis of AIDS. TNF-α and other cytokines can induce HIV expression in U1 cells. U1 cells also express HIV constitutively when grown to a relatively high density. AZT has been found not to be active in affecting HIV replication in chronically infected cell lines (Hsu et al., *Science* 254:1799–1802, 1991). An inhibitor of viral reverse transcriptase is expected to only protect new cells from becoming infected but not to affect viral production from cells already infected with HIV. Analysis by HIV-1 p24 antigen production in U1 cell culture media showed that CT2576 inhibited TNF-α, IL-6 mediated and the constitutive expression in U1 cells (FIG. 17) with no cytotoxicity using the trypan-blue dye exclusion assay. While TNF-α induces HIV expression through activation of NFκB, IL-6 and IL-1 also stimulates HIV expression through other pathways independent of NFκB activation in U1 cells.

EXAMPLE 12

Figure 18:
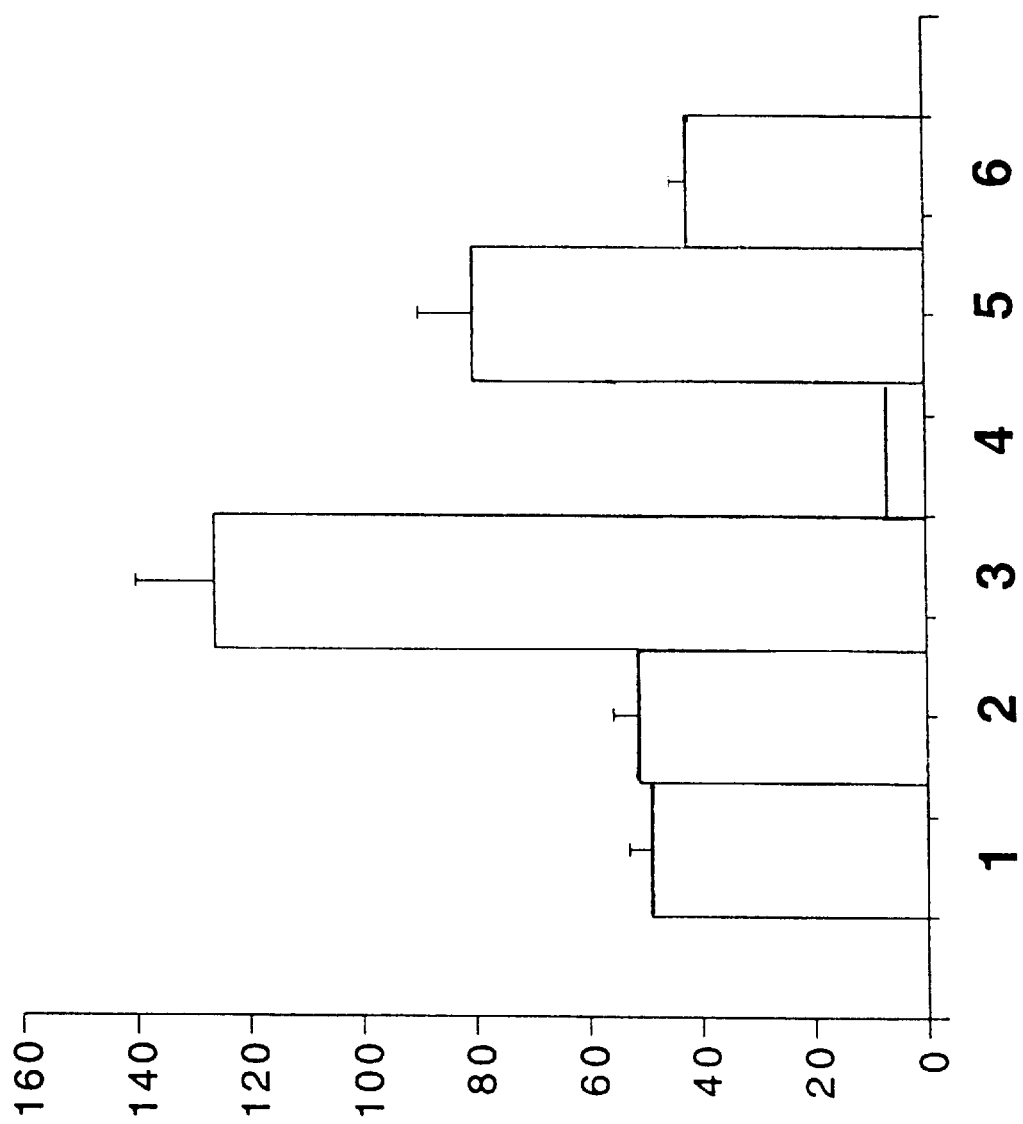
FIG. 18 shows a relationship between relative PA mass and activity of the compound CT3556. Transformed and serum-stimulated cells were measured for total PA mass according to the methods described herein. The tat-transfected cells stimulated with serum (col. 3) showed a significant increase in PA mass when compared with non-tat transfected cells stimulated with serum (col. 1). This increase in PA was blocked by administration of CT3556 10 $\mu$M. Similarly cells transfected with tar showed a significant drop in PA mass when treated with CT3556. The columns in FIG. 18 represent: (1) EB293 cells plus serum, (2) EB293 cells plus serum plus CT3556 (10 $\mu$M.), (3) 293tat cells plus serum, (4) 293tat cells plus serum plus CT3556 (10 $\mu$M.), (5) 293tar cells plus serum, and (6) 293tar cells plus serum plus CT3556 (10 $\mu$M.).
Figure 19:
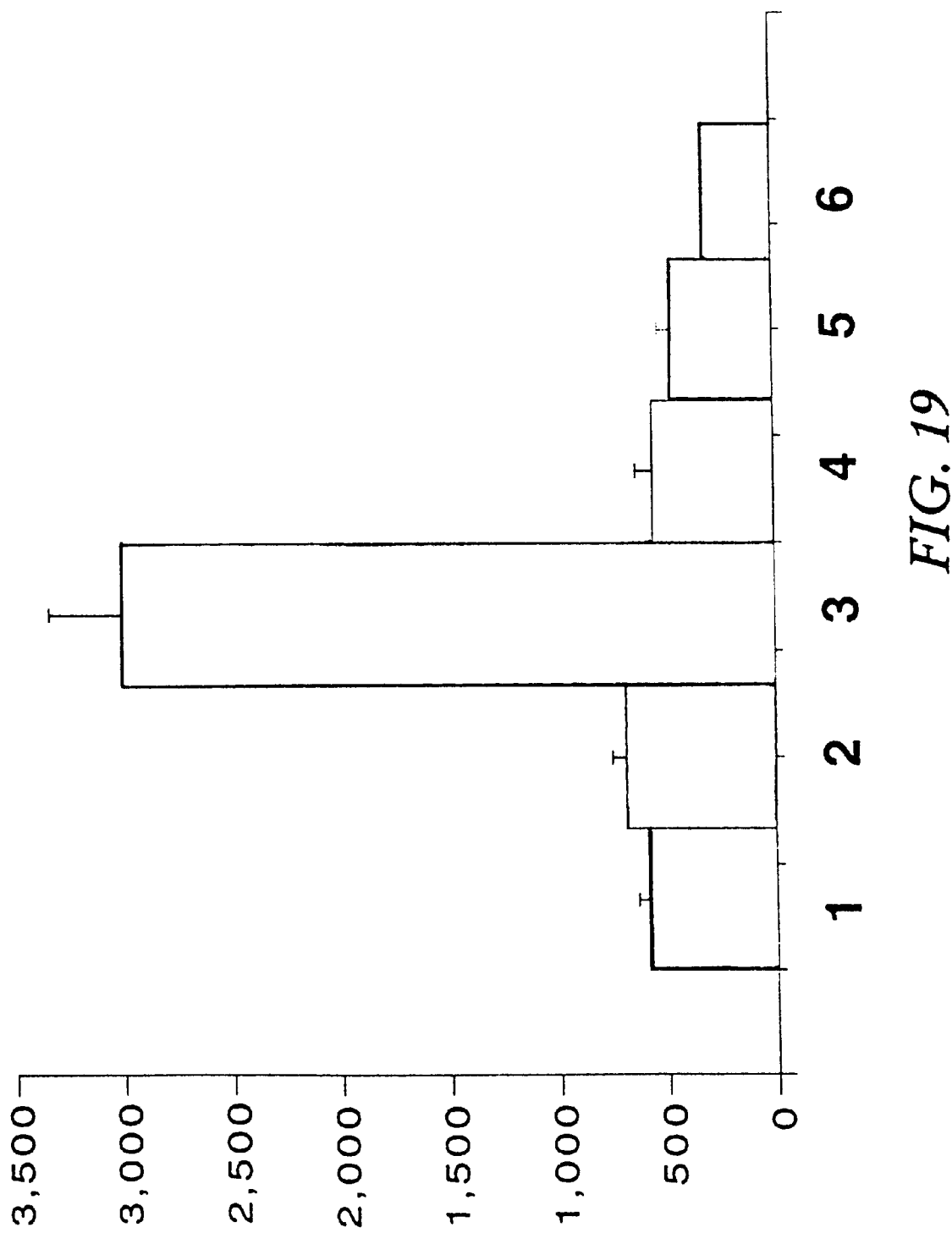
FIG. 19 shows the same experiment as in FIG. 18 only this time diacylglycerol was measured (DG). DG was assayed by collecting the DG HPLC peak (Rf 2–4.5 min) and verifying the predominance of DG species by mass spectroscopy analysis. The DG peak was integrated for a quantitative analysis. The six columns in FIG. 19 correspond to the same columns in FIG. 18.

This example illustrates that CT3556 and CT2576 inhibited myrPA formation in stimulated cells. FIGS. 18–21 show that both compounds (at a clinically achievable concentration of 10 μM) can inhibit myrPA formation in tat-transfected cells stimulated with serum. Specifically, FIG. 18 shows a relationship between relative PA mass and activity of the compound CT3556. Transformed and serum-stimulated cells were measured for total PA mass according to the methods described herein. The tat-transfected cells stimulated with serum (col. 3) showed a significant increase in PA mass when compared with non-tat transfected cells stimulated with serum (col. 1). This increase in PA was blocked by administration of CT3556 10 μM. Similarly cells transfected with tar showed a significant drop in PA mass when treated with CT3556. The columns in FIG. 18 represent: (1) EB293 cells plus serum, (2) EB293 cells plus serum plus CT3556 (10 μM.), (3) 293tat cells plus serum, (4) 293tat cells plus serum plus CT3556 (10μM.), (5) 293tar cells plus serum, and (6) 293tar cells plus serum plus CT3556 (10 μM.). FIG. 19 shows the same experiment as in FIG. 18 only this time diacylglycerol was measured (DG). DG was assayed by collecting the DG HPLC peak (Rf 2–4.5 min) and verifying the predominance of DG species by mass spectroscopy analysis. The DG peak was integrated for a quantitative analysis. The six columns in FIG. 19 correspond to the same columns in FIG. 18.

Figure 20:
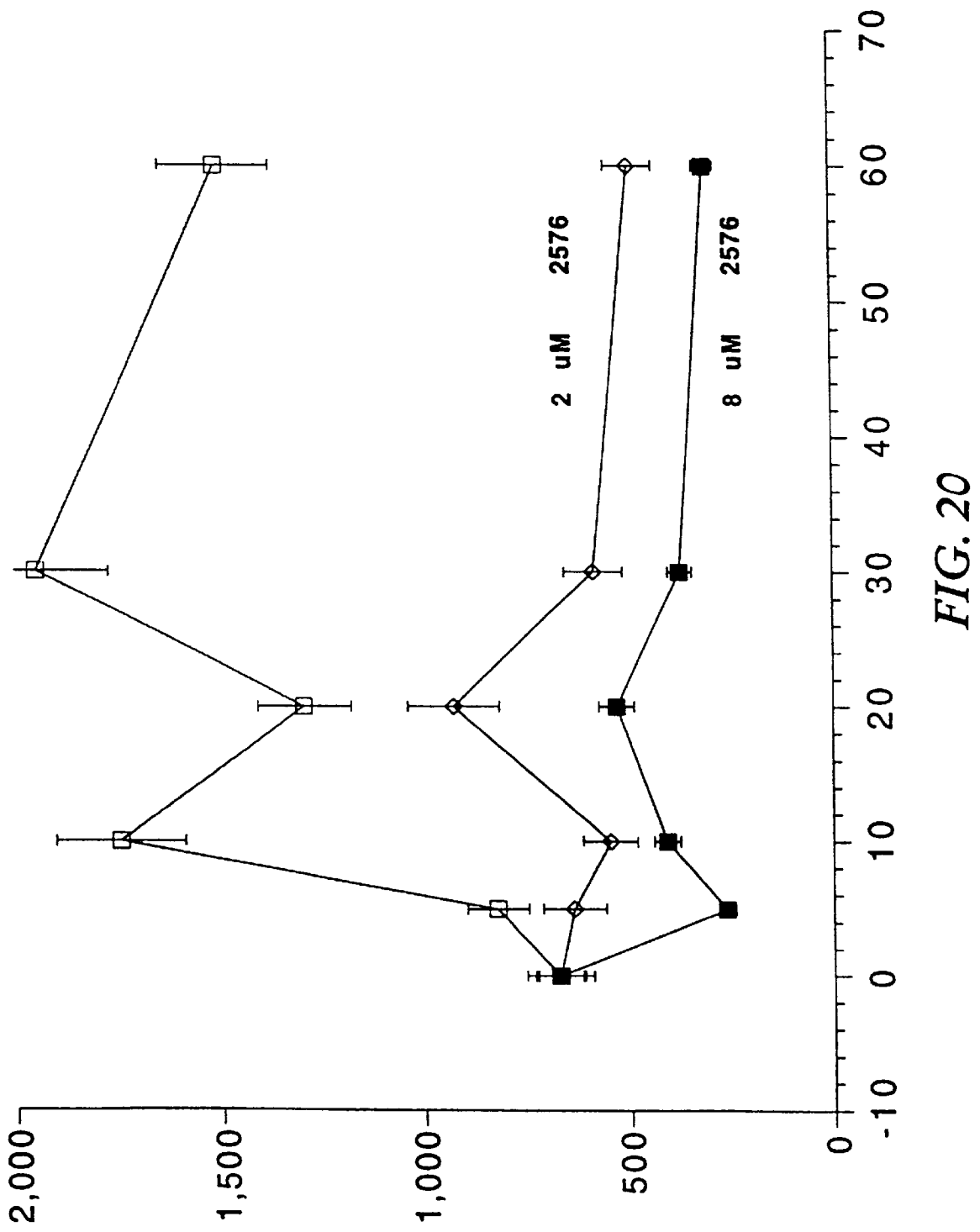
FIG. 20 shows a dose response relationship for CT2576 in inhibiting total PA mass in EB293 cells transfected with the tat expression plasmid and stimulated with serum. The time points for PA determinations were from 0 to one minute.

FIG. 20 shows a dose response relationship for CT2576 in inhibiting total PA mass in EB293 cells transfected with the tat expression plasmid and stimulated with serum. The time points for PA determinations were from 0 to one minute. FIG. 21 shows two graphs for peak D (a measure of various PA species in an HPLC separation) and Peak A5 (a measure of lyso (bis) PA species) with EB293 cells (human embryonic origin) stimulated with human TNF-α (20 ng/ml, Genzyme) with or without treatment with CT2576 (10 μM.). The left panel shows that drug treatment reduced PA mass across all time points measured, indicating inhibition of formation of PA species to acceleration of PA species metabolism. However, when considering the right hand graph showing increased lyso (bis) PA species across all time points, the CT2576 activity inhibits PA formation from lyso (bis) PA species.

We claim:

1. A method for treating viral infections and viral diseases, comprising administering an effective amount of a compound having a straight or branched aliphatic hydrocarbon structure of the general formula:

$$(X)j\text{-}R_4,$$

wherein j is an integer from one to three, and $R_4$ is a terminal moiety comprising a substituted or unsubstituted, carbocyclic or heterocyclic moiety or open chain analogs thereof, wherein the heterocyclic moiety consists essentially of one to three ring structures having 5–7 members each, a heteroatom, and a predominantly planar structure or essentially aromatic, and X is a racemic mixture or R or S enantiomer of:

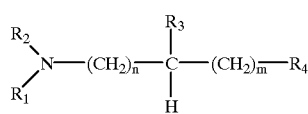

I wherein n is an integer from one to four and m is an integer from four to twenty, $R_1$ and $R_2$ are hydrogen, a straight or branched chain alkyl, alkenyl or alkynyl of up to twenty carbon atoms in length or $-(CH_2)_wR_5$, with the proviso that if $R_1$ or $R_2$ is $-(CH_2)_wR_5$, w is an integer from one to twenty and $R_5$ is an hydroxyl, halo, $C_{1-8}$ alkoxyl group or a substituted or unsubstituted carbocycle or heterocycle, or $R_1$ and $R_2$ may jointly form a substituted or unsubstituted, saturated or unsaturated heterocycle having from four to eight carbon atoms, N being a hetero atom of the resulting heterocycle, $R_3$ is hydrogen, a hydroxy group, a $C_{1-3}$ straight or branched alkyl, or a $C_{1-3}$ alkoxy, or X is independently a resolved enantiomer ω-1 secondary alcohol-substituted alkyl ($C_{5-8}$) substantially free of the other enantiomer, or X is a branched $-(CH_2)a\text{-}CHR_6-(CH_2)b\text{-}R_7$, wherein a is an integer from about 4 to about 12, b is an integer from 0 to 4, $R_6$ is an enantiomer (R or S) or racemic mixture ($C_{1-6}$) alkyl or alkenyl, and $R_7$ is a hydroxy, keto, cyano, chloro, iodo, fluoro, or chloro group.

2. The method of claim 1 that results in decreased expression of viral gene products.

3. The method of claim 1 wherein a total sum of carbon atoms comprising $R_1$ or $R_2$, $(CH_2)_n$ and $(CH_2)_m$ does not exceed forty.

4. The method of claim 1 wherein the viral infections are selected from the group consisting of: cytomegalovirus (CMV); herpes family of viruses; herpes simplex virus (HSV) 1, 2 and 6; hepatitis A, B, C and D; HIV 1 and 2; Epstein Barr virus (EBV); human T cell leukemia virus (HTLV); human papilloma virus (HPV); influenza; parainfluenza; respiratory syncytial virus; adenoviruses; rhinoviruses; and combinations thereof.

5. The method of claim 4 wherein the viral invection is CMV.

6. The method of claim 1 wherein the viral diseases are selected from the group consisting of: CMV retinitis; acquired immunodeficiency syndrome (AIDS); adult respiratory distress syndrome (ARDS); systemic viral diseases affecting immunocompromised individuals; cold sores genital herpes; genital warts; infectious mononucleosis; lymphomas; shingles; pericarditis; influenza, cold and flu; cachexia associated with HIV infection; cachexia associated with EBV infection; HIV, EBV and HTLV related malignancies; AIDS-related opportunistic infections, hepatitis; and combinations thereof.

7. A method of treating acquired immunodeficiency syndrome (AIDS) in human immunodeficiency virus (HIV) seropositive humans, comprising administering an effective amount of a compound having a straight or branched aliphatic hydrocarbon structure of the general formula:

$$(X)j\text{-}R_4,$$

wherein J is an integer from one to three, and $R_4$ is a terminal moiety comprising a substituted or unsubstituted, carbocyclic or heterocyclic moiety or open chain analogs thereof, wherein the heterocyclic moiety consists essentially of one to three ring structures having 5–7 members each, a heteroatom, and a predominantly planar structure or essentially aromatic, and X is a racemic mixture or R or S enantiomer of:

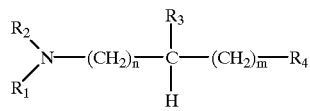

I wherein n is an integer from one to four and m is an integer from four to twenty, $R_1$ and $R_2$, are hydrogen, a straight or branched chain alkyl, alkenyl or alkynyl of up to twenty carbon atoms in length or $-(CH_2)_wR_5$, with the proviso that if R₁ or R₂, is —(CH₂)$_w$R₅, w is an integer from one to twenty and R₅ is an hydroxyl, halo, $C_{1-8}$ alkoxyl group or a substituted or unsubstituted carbocycle or heterocycle, or R₁ and R₂ may jointly form a substituted or unsubstituted, saturated or unsaturated heterocycle having from four to eight carbon atoms, N being a hetero atom of the resulting heterocycle, R₃ is hydrogen, a hydroxy group, a $C_{1-3}$ straight or branched alkyl, or a $C_{1-3}$ alkoxy, or X is independently a resolved enantiomer ω-1 secondary alcohol-substituted alkyl ($C_{5-8}$) substantially free of the other enantiomer, or X is a branched —(CH₂,)a-CHR₆—(CH₂) b-R₇, wherein a is an integer from about 4 to about 12, b is an integer from 0 to 4, R₆is an enantiomer (R or S) or racemic mixture ($C_{1-6}$) alkyl or alkenyl, and R₇is a hydroxy, keto, cyano, chloro, iodo, fluoro, or chloro group.

8. The method of claim 7 wherein a total sum of carbon atoms comprising R₁ or R₂, (CH₂)$_n$ and (CH₂)$_m$ does not exceed forty.

9. The method of claim 7 wherein R₅ is a substituted or unsubstituted aryl group wherein the substituted aryl group is mono, di or tri substituted with hydroxy, chloro, fluoro, bromo, or alkoxy (C1-6) substituents, or

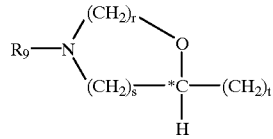

wherein R₉ is a hydrogen or a straight or branched chain alkane or alkene of up to eight carbon atoms in length, —(CH₂)$_m$R₅, or R₉ forms a cyclo saturated or unsaturated aromatic ring or substituted aromatic ring having from four to eight carbon atoms and including the nitrogen atom within the ring, r and s are independently integers from one to four, the sum (r+s) is not greater than five, wherein one or more carbon atoms in (CH₂)$_q$ or (CH₂)$_p$ may be substituted by a keto or hydroxy group, t is an integer from one to fourteen, and R₅ is a substituted or unsubstituted aryl group wherein the substituted aryl group is mono, di or tri substituted with hydroxy, chloro, fluoro, bromo, or alkoxy (C1-6) substituents.

10. The method of claim 7 wherein R₄ is selected from the group consisting of substituted or unsubstituted acridinyl; acridonyl; alkylpyridinyl; anthraquinonyl; ascorbyl; azaazulenyl; azabenzanthracenyl; azabenzanthrenyl; azabenzophenanthrenyl; azachrysenyl; azacyclazinyl; azaindolyl; azanaphthacenyl; azanaphthalenyl; azapyrenyl; azatriphenylenyl; azepinyl; azinoindolyl; azinopyrrolyl; benzacridinyl; benzazapinyl; benzamidyl; benzofuryl; benzonaphthyridinyl; benzopyranonyl; benzopyranyl; benzopyronyl; benzoquinolinyl; benzoquinolizinyl; benzothiepinyl; benzothiophenyl; benzylisoquinolinyl; biotinyl; bipyridinyl; butenolidyl; butyrolactonyl; caprolactamyl; carbazolyl; carbolinyl; catechinyl; chromenopyronyl; chromonopyranyl; coumarinyl; coumaronyl; decahydroquinolinyl; decahydroquinolonyl; diazaanthracenyl; diazaphenanthrenyl; dibenzazepinyl; dibenzofuranyl; dibenzothiophenyl; dichromylenyl; dihydrofuranyl; dihydroisocoumarinyl; dihydroisoquinolinyl; dihydropyranyl; dihydropyridinyl; dihydropyridonyl; dihydropyronyl; dihydrothiopyranyl; diprylenyl; dioxanthylenyl; enantholactamyl; flavanyl; flavonyl; fluoranyl; fluorescienyl; flutarimidyl; furandionyl; furanochromanyl; furanonyl; furanoquinolinyl; furanyl; furopyranyl; furopyronyl; glutarimidyl; heteroazulenyl; hexahydropyrazinoisoquinolinyl; homopthalamidyl; hydrofuranyl; hydrofurnanonyl; hydroindolyl; hydropyranyl; hydropyridinyl; hydropyrrolyl; hydroquinolinyl; hydrothiochromenyl; hydrothiophenyl; imidizoamidyl; indolizidinyl; indolizinyl; indolonyl; isatinyl; isatogenyl; isobenzofurandionyl; isobenzofuranyl; isochromanyl; isoflavonyl; isoindolinyl; isoindolobenzazepinyl; isoindolyl; isoquinolinyl; isoquinuclidinyl; lactamyl; lactonyl; maleimidyl; monoazabenzonaphthenyl; naphthalenyl; naphthimidazopyridinedionyl; naphthindolizinedionyl; naphthodihydropyranyl; naphthofuranyl; naphthothiophenyl; naphthyridinyl; oxepinyl; oxindolyl; oxolenyl; perhydroazolopyridinyl; perhydroindolyl; phenanthraquinonyl; phenanthridinyl; phenanthrolinyl; phthalideisoquinolinyl; phthalimidyl; phthalonyl; piperidinyl; piperidonyl; prolinyl; pyradinyl; pyranoazinyl; pyranoazolyl; pyranopyrandionyl; pyranopyridinyl; pyranoquinolinyl; pyranopyradinyl; pyranyl; pyrazolopyridinyl; pyridinethionyl; pyridinonaphthalenyl; pyridinopyridinyl; pyridinyl; pyridocolinyl; pyridoindolyl; pyridopyridinyl; pyridopyrimidinyl; pyridopyrrolyl; pyridoquinolinyl; pyronyl; pyrrocolinyl; pyrrolamidinyl; pyrrolidinyl; pyrrolizidinyl; pyrrolizinyl; pyrrolodiazinyl; pyrrolonyl; pyrrolopyrimidinyl; pyrroloquinolonyl; pyrrolyl; quinacridonyl; quinolinyl; quinolizidinyl; quinolizinyl; quinolonyl; quinuclidinyl; rhodaminyl; spirocoumaranyl; succinimidyl; sulfolanyl; sulfolenyl; tetrahydrofuranyl; tetrahydroisoquinolinyl; tetrahydropyranyl; tetrahydropyridinyl; tetrahydrothiapyranyl; tetrahydrothiophenyl; tetrahydrothiopyranonyl; tetrahydrothiopyranyl; tetronyl; thiabenzenyl; thiachromanyl; thiadecalinyl; thianaphthenyl; thiapyranyl; thiapyronyl; thiazolopyridinyl; thienopryidinyl; thienopyrrolyl; thienothiophenyl; thiepinyl; thiochromenyl; thiocoumarinyl; thiophenyl; thiopyranyl; triazaanthracenyl; triazinoindolyl; triazolopyridinyl; tropanyl; xanthenyl; xanthonyl, xanthydrolyl, adeninyl; alloxanyl; alloxazinyl; anthranilyl; azabenzanthrenyl; azabenzonaphthenyl; azanaphthacenyl; azaphenoxazinyl; azapurinyl; azinyl; azoloazinyl; azolyl; barbituric acid; benzazinyl; benzimidazolethionyl; benzimidazolonyl; benzimidazolyl; benzisothiazolyl; benzisoxazolyl; benzocinnolinyl; benzodiazocinyl; benzodioxanyl; benzodioxolanyl; benzodioxolyl; benzopyridazinyl; benzothiazepinyl; benzothiazinyl; benzothiazolyl; benzoxazinyl; benzoxazolinonyl; benzoxazolyl; cinnolinyl; depsidinyl; diazaphenanthrenyl; diazepinyl; diazinyl; dibenzoxazepinyl; dihydrobenzimidazolyl; dihydrobenzothiazinyl; dihydrooxazolyl; dihydropyridazinyl; dihydropyrimidinyl; dihydrothiazinyl; dioxanyl; dioxenyl; dioxepinyl; dioxinonyl; dioxolanyl; dioxolonyl; dioxopiperazinyl; dipyrimidopyrazinyl; dithiolanyl; dithiolenyl; dithiolyl; flavinyl; furopyrimidinyl; glycocyamidinyl; guaninyl; hexahydropyrazinoisoquinolinyl; hexahydropyridazinyl; hydantoinyl; hydroimidazolyl; hydropyrazinyl; hydropyrazolyl; hydropyridazinyl; hydropyrimidinyl; imidazolinyl; imidazolyl; imidazoquinazolinyl; imidazothiazolyl; indazolebenzopyrazolyl; indoxazenyl; inosinyl; isoalloxazinyl; isothiazolyl; isoxazolidinyl; isoxazolinonyl; isoxazolinyl; isoxazolonyl; isoxazolyl; lumazinyl; methylthyminyl; methyluracilyl; morpholinyl; naphthimidazolyl; oroticyl; oxathianyl; oxathiolanyl; oxazinonyl; oxazolidinonyl; oxazolidinyl; oxazolidonyl; oxazolinonyl; oxazolinyl; oxazolonyl; oxazolopyrimidinyl; oxazolyl; perhydrocinnolinyl; perhydropyrroloazinyl; perhydropyrrolooxazinyl; perhydropyrrolothiazinyl; perhydrothiazinonyl; perimidinyl; phenazinyl; phenothiazinyl; phenoxathiinyl; phenoxazinyl; phenoxazonyl; phthalazinyl; piperazindionyl; piperazinodionyl; polyquinoxalinyl; pteridinyl; pterinyl; purinyl; pyrazinyl; pyrazolidinyl; pyrazolidonyl; pyrazolinonyl; pyrazolinyl; pyrazolobenzodiazepinyl; pyrazolonyl; pyrazolopyridinyl; pyrazolopyrimidinyl; pyrazolotriazinyl; pyrazolyl; pyridazinyl; pyridazonyl; pyridopyrazinyl; pyridopyrimidinyl; pyrimidinethionyl; pyrimidinyl; pyrimidionyl; pyrimidoazepinyl; pyrimidopteridinyl; pyrrolobenzodiazepinyl; pyrrolodiazinyl; pyrrolopyrimidinyl; quinazolidinyl; quinazolinonyl; quinazolinyl; quinoxalinyl; sultamyl; sultinyl; sultonyl; tetrahydrooxazolyl; tetrahydropyrazinyl; tetrahydropyridazinyl; tetrahydroquinoxalinyl; tetrahydrothiazolyl; thiazepinyl; thiazinyl; thiazolidinonyl; thiazolidinyl; thiazolinonyl; thiazolinyl; thiazolobenzimidazolyl; thiazolyl; thienopyrimidinyl; thiazolidinonyl; thyminyl; triazolopyrimidinyl; uracilyl; xanthinyl; xylitolyl, azabenzonaphthenyl; benzofuroxanyl; benzothiadiazinyl; benzotriazepinonyl; benzotriazolyl; benzoxadizinyl; dioxadiazinyl; dithiadazolyl; dithiazolyl; furazanyl; furoxanyl; hydrotriazolyl; hydroxytrizinyl; oxadiazinyl; oxadiazolyl; oxathiazinonyl; oxatriazolyl; pentazinyl; pentazolyl; petrazinyl; polyoxadiazolyl; sydononyl; tetraoxanyl; tetrazepinyl; tetrazinyl; tetrazolyl; thiadiazinyl; thiadiazolinyl; thiadiazolyl; thiadioxazinyl; thiatriazinyl; thiatriazolyl; thiatriazolyl; triazepinyl; triazinoindolyl; triazinyl; triazolinedionyl; triazolinyl; triazolyl; trioxanyl; triphenodioxazinyl; triphenodithiazinyl; trithiadiazepinyl; trithianyl; and trixolanyl.

11. The method of claim 7 wherein $R_4$ is selected from the group consisting of dimethylxanthinyl, methylxanthinyl, phthalimidyl, homophthalimidyl, methylbenzoyleneureayl, quinazolinonyl, octylcarboxamidobenzenyl, methylbenzamidyl, methyldioxotetrahydropteridinyl, glutarimidyl, piperidonyl, succinimidyl, dimethoxybenzenyl, methyldihydrouracilyl, methyluracilyl, methylthyminyl, piperidinyl, dihydroxybenzenyl, methylpurinyl, 1,3-cyclohexanedione, 1,3-cyclopentanedione, 1,3-dihydroxynaphthalene, 1-methyllumazine, methylbarbituric acid, 3,3-dimethylflutarimide, 2-hydroxypyridine, methyldihydroxypyrazolopyrimidine, 1,3-dimethyldihydroxypyrazolo[4,3-d]pyrimidine, methylpyrrolopyrimidine, 1-methylpyrrolo [2,3-d] pyrimidine, 2-pyrrole amides, 3-pyrrole amides, 1,2,3,4-tetrahydroisoquinolone, 1-methyl-2,4(1H,3H)-quinazolinedione (1-methylbenzoyleneurea, quinazolin-4 (3H)-one, alkyl-substituted ($C_{1-6}$) thymine, methylthymine, alkyl-substituted ($C_{1-6}$) uracil, 6-aminouracil, 1-methyl-5,6-dihydrouracil, 1-methyluracil, 5- and/or 6-position substituted uracils, 1,7-dimethylxanthine, 3,7-dimethylxanthine, 3-methylxanthine, 3-methyl-7-methylpivaloylxanthine, 8-amino-3-methylxanthine, 7-methylhypoxanthine, 3,7-dimethylxanthine, 3-methylxanthine, 3-methyl-7-methylpivaloylxanthine, 8-amino-3-methylxanthine, 7-methylhypoxanthine, 1-methyluracil, 1-methylthymine, 1-methyl-5,6-dihydrouracil, glutarimides, phthalimide, pteridine, 1-methyl-2,4(1H,3H)-quinazolinedione (1-methylbenzoyleneurea), 6-aminouracil, homophthalimide, succinimide, 1,3-cyclohexanedione, resorcinol, 1,3-dihydroxynaphthalene, 1,3-cyclopentanedione, 1,3-dimethyldihydroxypyrazolo[4,3-d] pyrimidine, 5-substituted uracils, 6-substituted uracils, 1-methylpyrrolo[2,3-d]pyrimidine, 1-methyllumazine, imidazole amides, 2-pyrrole amides, 3-pyrrole amides, benzamides, methylbarbituric acid, benzene, piperdine, delta-lactam, 2-hydroxypyridine, 1,2,3,4-tetrahydroisoquinolone, isocarbostyril, and quinazolin-4 (3H)-one.

12. The method of claim 7 wherein the compound is selected from the group consisting of 1-(11-hexylamino-8-hydroxyundecyl)-3,7-dimethylxanthine, N-(11-phenylamino-10-hydroxundecyl)-3,7-dimethylxanthine, 1-(11-octylamino-10-hydroxyundecyl)-3,7-dimethylxanthine, 1-(11-N-octylaminoundecyl)-3,7-dimethylxanthine, 1-[11-(N-ocylacetamido)-10-acetoxyundecyl]-3,7-dimethylxanthine, 1-(9-(2-hydroxydecyl-1-amino)nonyl)-3,7-dimethylxanthine, R-1-(5-hydroxyhexyl)-3,7-dimethylxanthine, N-(11-octylamino-10-hydroxyundecyl)-homophthalimide, N-(11-octylamino-10-hydroxyundecyl)-3-methylxanthine, N-(11-octylamino-10-hydroxyundecyl)-2-piperdone, 3-(11-octylamino-10-hydroxyundecyl)-1-methyluracil, 3-(11-octylamino-10-hydroxyundecyl)-1-methyldihydrouracil, 1-(9-decylamino-8-hydroxynonyl)-3,7-dimethylxanthine, 1-(9-dodecylamino-8-hydroxynonyl)-3,7-dimethylxanthine, and combinations thereof.

13. The method of claim 7 that results in decreased expression of HIV gene products.

14. The method of claim 7 that results in decreased release of HIV p24 antigen.

* * * * *